United States Patent [19]

Stephanopoulos et al.

[11] Patent Number: 5,510,262

[45] Date of Patent: * Apr. 23, 1996

[54] CELL-CULTURING APPARATUS AND METHOD EMPLOYING A MACROPOROUS SUPPORT

[75] Inventors: Gregory Stephanopoulos, Winchester; Rahul Singhvi, Cambridge; Seujeung Park, Somerville; Maria Flytzani-Stephanopoulos, Winchester, all of Mass.; Mark A. Applegate, San Diego, Calif.

[73] Assignee: Massachusetts Institute of Technology, Cambridge, Mass.

[*] Notice: The portion of the term of this patent subsequent to Nov. 16, 2010, has been disclaimed.

[21] Appl. No.: 153,204

[22] Filed: Nov. 16, 1993

Related U.S. Application Data

[63] Continuation of Ser. No. 921,920, Jul. 29, 1992, Pat. No. 5,262,320, which is a continuation-in-part of Ser. No. 539,861, Jun. 18, 1990, abandoned, and Ser. No. 789,289, Nov. 8, 1991, abandoned.

[51] Int. Cl.[6] ............................... C12M 3/00; C12N 5/00
[52] U.S. Cl. ............................... 435/240.23; 435/240.241; 435/297.2; 435/299.1
[58] Field of Search .................. 435/240.23, 41, 435/283, 240.1, 240.2, 284, 283, 287, 176, 180, 182, 240.241, 240, 242, 818, 289.1, 297.2, 297.4, 299.1

[56] References Cited

U.S. PATENT DOCUMENTS

| | | | |
|---|---|---|---|
| 4,153,510 | 5/1979 | Messing et al. | 195/59 |
| 4,537,860 | 8/1985 | Tolbert et al. | 435/240 |
| 4,757,017 | 7/1988 | Cheung | 435/240.23 |
| 4,789,634 | 12/1988 | Muller-Lierheim et al. | 435/288 |
| 4,833,083 | 5/1989 | Saxena | 435/240.24 |
| 4,919,895 | 4/1990 | Heldebrant et al. | 422/129 |
| 4,948,728 | 8/1990 | Stephanopoulos et al. | 435/41 |
| 4,987,068 | 1/1991 | Trosch et al. | 435/176 |
| 5,037,749 | 8/1991 | Findlay | 435/176 |
| 5,057,428 | 10/1991 | Mizutani et al. | 435/285 |
| 5,081,035 | 1/1992 | Halberstadt et al. | 435/284 |
| 5,096,814 | 3/1992 | Aivasidis et al. | 435/176 |
| 5,262,320 | 11/1993 | Stephanopoulos et al. | 435/240.23 |

FOREIGN PATENT DOCUMENTS

| | | |
|---|---|---|
| 1086870A | 3/1989 | Japan. |
| WO86/05811 | 10/1986 | WIPO. |

OTHER PUBLICATIONS

Racher et al., "Studies on Monoclonal Antibody Production By A Hybridoma Cell Line (C1E3) Immobilized in a Fixed Bed, Porosphere Culture System," *Eng. Conf. on Cell Culture at Santa Barbara, Calif.,* (Dec. 3–8, 1989).

(List continued on next page.)

*Primary Examiner*—William H. Beisner
*Attorney, Agent, or Firm*—Hamilton, Brook, Smith & Reynolds

[57] ABSTRACT

An apparatus and method are disclosed for culturing cells by flowing a medium through a packed bed of biocompatible macroporous ceramic particles disposed in a cell-culture reactor. In one embodiment, oxygen and other nutrients in the medium are transported significantly by convective flow through pores of the biocompatible macroporous ceramic particles to cells disposed within the pores. Oxygen can be introduced to the cell-culture reactor by sparging oxygen gas into the cell-culture reactor. Oxygen content in the medium can also be increased by increasing the solubility of oxygen in the medium, such as by adding perfluorocarbon or other oxygen carriers to the medium. The oxygen capacity of the reactor can be further increased by sparging oxygen-containing gas into the medium at a plurality of points in the packed bed, or by introducing oxygen gas to the medium through a solid-phase oxygen gas-permeable membrane disposed in the packed bed. Alternatively, an oxygen-containing gas can be directed through an oxygen-permeable conduit disposed within at least one passage of a biocompatible macroporous support.

18 Claims, 10 Drawing Sheets

OTHER PUBLICATIONS

Stephanopoulos et al., "The Effect of Intraparticle Convection on Nutrient Transport in Porous Biological Pellets", *Chem. Eng. Science,* 44:2031–2039 (1989).

Tsiveriotis, "Convection Inside a Porous Microbial Particle As a Means of Nutrient Transport", Masters' Thesis, Massachusetts Institute of Technology (1988).

Stephanopoulos, et al., "Porous Microcarriers for Cell Culture" 9:74 (1989).

Lyderson, "Perfusion Cell Culture System Based on Ceramic Matrices", 170–192 (1987).

ns Ser. No. 07/921,
920, filed Jul. 29, 1992, now U.S. Pat. No. 5,262,320, which
is a Continuation-in-Part application Ser. No. 07/539,861,
filed Jun. 18, 1990, now abandoned, and a Continuation-in-
Part of application Ser. No. 07/789,289, filed Nov. 8, 1991,
now abandoned.

BACKGROUND OF THE INVENTION

Cells are often cultured in reactors for generation of useful cell products, such as anti-bodies. In order to maintain a cell culture, oxygen and other nutrients generally must be supplied to the cells. Cell cultures are usually maintained in reactors by perfusion, wherein a cell culture medium, including oxygen and other nutrients, is directed through the cell-culture reactor.

However, cell-culture reactors which are currently in use often suffer from other types of problems. They typically can support only small cell loadings per unit of reactor volume. Also, they can operate only within a small window of flow or agitation rates and they usually require other cell-retention devices (i.e. filters) in order to be able to operate in a perfusion mode. Their capacity in sparingly soluble nutrients, such as oxygen, is small, and as a result, scale-up problems are not easy to solve. For the case of beds of substrates, the height of beds is limited by the solubility of oxygen in the medium directed through the cell culture.

One specific problem is that use of porous particles as substrates for perfused cell cultures has been limited. The supply of nutrients, and, in particular, of oxygen, is thereby limited due to small rates at which such nutrients are transported by diffusion from the bulk to the interior of the particle where cells typically reside. As a result, the total number of cells that can be supported by diffusive nutrient supply is small and their production capability usually low. Further, the density of cells within the pores has been difficult to control because the rate of diffusion into the pores generally is not significantly affected by the rate of flow of medium through the interstitial passages. Non-porous microcarriers have no such transport limitations, however, their applicability is seriously impaired by high sensitivity to shear, low cell densities and low bioreactor productivities.

Further, suitable media for culturing cells typically exhibit a limited solubility of oxygen, thereby causing medium directed through a cell culture reactor to be depleted of oxygen prior to depletion of other nutrients. Cell-culture reactor systems, therefore, generally have included recycling of the medium through a remote reservoir in order to replenish the oxygen content of the medium. Medium is typically recycled in order to obtain a concentration of product in the medium which can be processed from the medium cost-effectively, and also to increase the amount of product per unit volume of spent medium.

However, cell productivity is limited in recycle-type reactors because medium which is recycled through the remote reservoir often cannot be treated to remove cell waste-products which exhibit toxicity to the cell culture. The productivity per cell in the cell culture of desired products is thereby diminished as waste products accumulate in the medium which is recirculated through the cell culture and the cell culture reactor.

There have been many attempts to increase the concentration of oxygen in medium directed through cell culture reactors. However, most methods have suffered from various types of problems. For example, increasing the rate of oxygen supplied to a cell culture reactor by increasing the rate of medium flow through the cell culture reactor is limited by the high sensitivity of cells to shear forces resulting from the increased rate of medium flow. Sparging of oxygen directly into a cell culture reactor is usually unacceptable, especially for mammalian cell cultures, because of the susceptibility of such cultures to detrimental proximate hydrodynamic forces and excessive foaming of the medium as a consequence of sparging. In another example, perfluorocarbons have been introduced to a medium in order to increase the solubility of oxygen in the medium. However, perfluorocarbons must be separated from the medium prior to recovery of cell products, thereby introducing an additional processing step which can reduce productivity and add expense to the operation of cell-culture reactors.

Entrapment of cells within pores of a macroporous support in order to protect cells from damaging shearing forces allows faster rates of medium flow through a cell culture reactor. However, in the absence of fluid flow through the pores of the support, transport of oxygen and other nutrients to cells can be limited by the process of diffusion. Also, although enabling a larger cell culture reactor, the medium must still be recycled in order to attain better medium utilization and cost-effective concentrations of cell product, thereby resulting in introduction of medium to the cell culture which contains a significant amount of cell waste-products.

A need exists, therefore, for a new method and apparatus for culturing cells which overcome or minimize the aforementioned problems.

SUMMARY OF THE INVENTION

The present invention relates to a new cell-culture apparatus and a new method for culturing cells.

One embodiment of the apparatus for culturing cells includes a cell-culture reactor and a packed bed of biocompatible macroporous ceramic particles, the packed bed being disposed within the cell-culture reactor. The biocompatible macroporous ceramic particles have pores which extend through the biocompatible porous ceramic particles. The pores have an average pore diameter sufficient to allow cells of a cell culture to collect within the pores. Suitable means pass a medium containing oxygen through the packed bed so as to provide oxygen and other nutrients to the cell culture in amounts sufficient to culture the cells. At least a portion of the medium within the cell-culture reactor is directed through the pores at a rate and in an amount sufficient to provide to the cells by convective flow of the medium through the pores a sufficient portion of the oxygen and other nutrients consumed by the cells to maintain the viability of the cell culture.

In another embodiment, the apparatus for culturing cells includes a cell-culture reactor having a cell-culture medium inlet and cell-culture medium outlet. A biocompatible macroporous support defines at least one passage. The biocompatible macroporous support is disposed within the cell-culture reactor between the medium inlet and the medium outlet. The biocompatible macroporous support includes pores which have a pore diameter sufficient to allow cells of the cell culture to collect within the pores and to allow oxygen and other nutrients to migrate from the passage into the pores for consumption by the cells. At least one oxygen-permeable conduit is disposed within the passage, whereby oxygen in an oxygen-containing gas directed through the oxygen-permeable conduit migrates from the oxygen-containing gas across an oxygen-permeable wall of the oxygen-permeable conduit to cell-culture medium and is dissolved in the nutrient-containing medium directed through the passage, thereby allowing oxygen to migrate from the passage to the cell culture within the pores of the biocompatible macroporous support. Suitable means direct the oxygen-containing gas through the oxygen-permeable conduit, whereby oxygen migrates across the oxygen-permeable wall of the oxygen-permeable conduit to the cell-culture medium which is being directed through the passage within the cell-culture reactor. Suitable means direct the cell culture medium from the medium inlet through the passage within which the oxygen-permeable conduit is disposed and out of the cell-culture reactor at the medium outlet at a rate sufficient to provide nutrients to the cells in the pores of the biocompatible macroporous support in an amount sufficient to culture the cells.

In one embodiment of the method, a packed bed is inoculated with cells to establish a cell culture. The packed bed comprises biocompatible macroporous ceramic particles having pores extending through the biocompatible macroporous ceramic particles. A medium, containing oxygen and other nutrients, is flowed through the packed bed and the cell culture at a rate sufficient to direct at least a portion of the medium through the pores at a rate and in an amount sufficient to provide oxygen and other nutrients to the cells disposed in the pores, whereby a sufficient portion of the oxygen and other nutrients consumed by the cells to maintain the viability of the cells are provided to the cells by convective flow of the medium through the pores.

In another embodiment of the method, a biocompatible macroporous support is inoculated with cells, wherein the biocompatible macroporous support is disposed within a cell-culture reactor having a cell-culture medium inlet and a cell-culture medium outlet. The biocompatible macroporous support defines at least one passage between the medium inlet and the medium outlet. The biocompatible macroporous support includes pores having a pore diameter sufficient to allow cells to collect within the pores and to allow oxygen and other nutrients to migrate from the passage into the pores for consumption by the cells. A cell-culture medium is directed into the medium inlet at a rate sufficient to provide nutrients to the cells in the pores of the biocompatible macroporous support in an amount sufficient to culture the cells. An oxygen-containing gas is directed through an oxygen-permeable conduit disposed within the passage, whereby oxygen in the oxygen-containing gas migrates across an oxygen-permeable wall of the oxygen-permeable conduit to the cell-culture medium which is being directed through the passage. Oxygen is thereby allowed to migrate from the passage to the cell culture within the pores of the biocompatible macroporous support at a rate sufficient to culture the cells.

The invention has many advantages. For example, convective flow through a packed bed of biocompatible macroporous ceramic particles significantly increases the rate and the amount of medium flow through the pores of the biocompatible macroporous ceramic particles. Control of cell density and of cell activity in cell cultures can therefore be effected by controlling the rate and the amount of oxygen and other nutrients provided to the cells. Further, cells within the pores of the ceramic particles are protected from shear stresses caused by flow of the medium through interstitial passages formed between the biocompatible macroporous ceramic particles of the packed bed, thereby allowing a greater flow rate of medium through the packed bed. The medium can also be oxygenated by various methods which increase agitation of the medium conducted through the interstitial passages, such as by sparging oxygen or other oxygen-containing gas into the cell-culture reactor. Convection through the pores of the biocompatible macroporous ceramic particles thereby allows in situ oxygenation, whereby oxygen dissolves in the medium from gaseous bubbles as dissolved oxygen is consumed by cells within the pores. Also, larger columns, having greater cell densities, can be operated, for example, by transferring oxygen into the packed bed, by means of oxygen gas-permeable membranes immersed in the packed bed and by increasing the solubility of oxygen in the medium, such as by adding perfluorocarbon or other carriers to the medium.

In addition, dissolving oxygen within a cell-culture reactor from an oxygen-permeable conduit into a passage defined by a biocompatible macroporous support allows effective medium utilization and enables formation of cost-effective concentrations of cell product in spent medium without substantial recycling of the spent medium. Also, productivity of the cell culture is significantly increased by elimination of recycling of spent medium because the concentration of cell waste products in medium proximate to cells at the medium inlet of the cell culture reactor is substantially reduced. Further, the concentration of cell products in the spent medium generated by the cell-culture in the cell-culture system is significantly higher than most cell-culturing reactors, thereby diminishing the volume of medium required to operate the cell-culture reactors. Therefore, the amount of spent medium that must be separated from the cell product is substantially reduced. Also, the velocity of nutrient-containing medium directed through the cell culture reactor is substantially reduced, thereby allowing cells formed in the cell culture, which are not anchorage-dependent and which become dislodged from the biocompatible macroporous support, to settle within the cell-culture reactor. These cells can be removed from the cell-culture reactor and collected for analysis without interruption of flow of medium through the cell-culture reactor. Further, introduction of oxygen to medium within the cell-culture reactor reduces the dependency of the cell culture on the low solubility of oxygen in the medium. Cell-culture reactors can be designed wherein the medium is supplemented by fresh nutrients at various points along the length of the reactor between the medium inlet and medium outlet for treatment, such as adjustment of pH or introduction of additional nutrients, and then reintroduced along the path of flow of medium within the cell-culture reactor. Cell-culture reactors can, therefore, be constructed which are substantially larger than reactors in which cell density and productivity is dependent upon the solubility of oxygen in the medium. Also, lack of a need for an external oxygenator substantially reduces suspension cell lysis which typically occurs by pumping cells through a pump.

DETAILED DESCRIPTION OF THE INVENTION

The features and other details of the apparatus and method of the invention will now be more particularly described with reference to the accompanying drawings and pointed out in the claims. The same number present in different figures represents the same item. It will be understood that the particular embodiments of the invention are shown by way of illustration and not as limitations of the invention. The principal features of this invention can be employed in various embodiments without departing from the scope of the invention.

Figure 1:
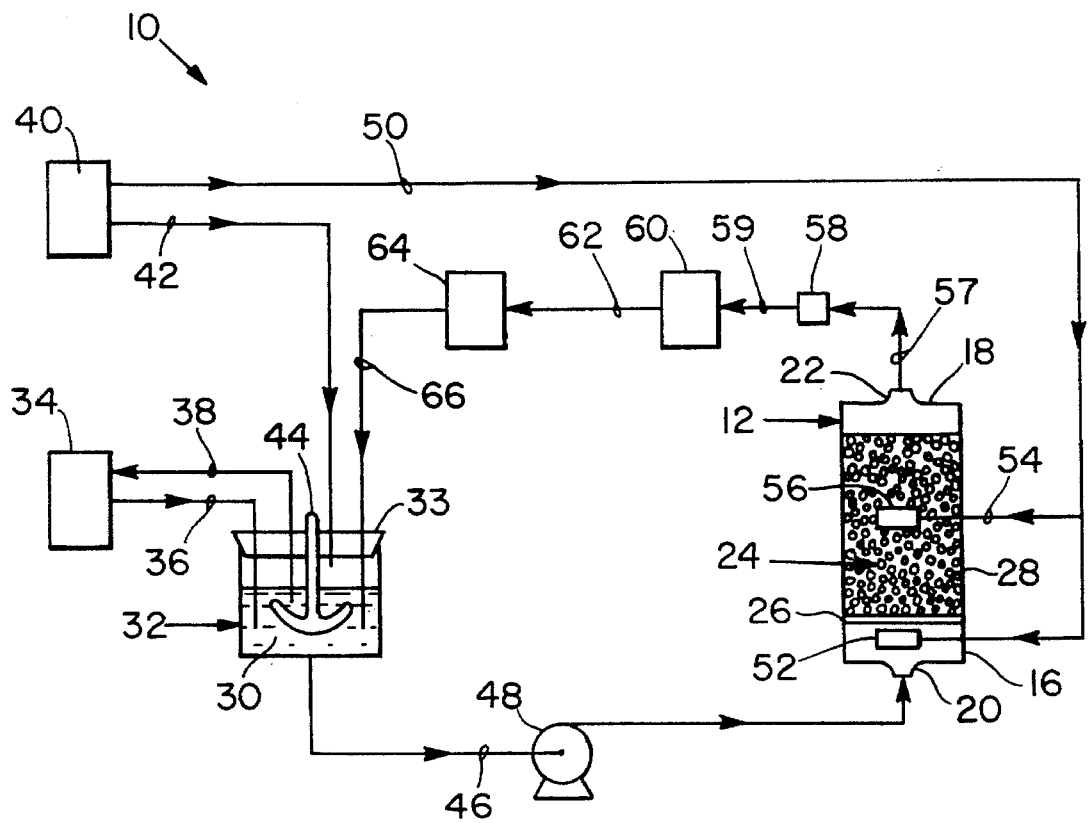
FIG. 1 is a schematic illustration of one embodiment of a cell-culturing system of the invention.

In a preferred embodiment of the present invention, cell-culture system 10, illustrated in FIG. 1, includes cell-culture reactor 12. Cell culture reactor 12 has an inlet end 16 and an outlet end 18. Cell-culture reactor 12 is constructed of a suitable material, such as glass, steel, etc. Inlet 20 is disposed at inlet end 16 of cell-culture reactor 12 for directing a suitable medium into cell-culture reactor 12. Outlet 22 is disposed at outlet end 18 of cell-culture reactor 12 for directing medium out of cell-culture reactor 12.

Packed bed 24 is disposed within cell-culture reactor 12 and can be supported within cell culture reactor 12 by a suitable means, such as by grid 26. Packed bed 24 is formed of biocompatible macroporous ceramic particles 28. Biocompatible macroporous ceramic particles 28 can fill or only partially fill cell-culture reactor 12. Biocompatible macroporous ceramic particles 28 are suitable for inoculation with a suitable cell culture. "Biocompatible," as that term is used herein, means that the cells of interest will survive and/or grow attached to or in the presence of the particles and that desired characteristics of the cells will not be significantly diminished.

Ceramic, as that term is used herein, means inorganic nonmetallic materials including, for example, pottery, porcelain, refractories, structural clay materials, abrasives, glass ferroelectrics, etc. Preferred ceramic materials include oxides of the elements of groups IIa, IIIa and IVa, mixed oxides of these elements, and ceramic compounds of group IIa, IIIa and IVa elements. It is to be understood that biocompatible macroporous ceramic particles can also comprise the above biocompatible ceramics and biocompatible dopants of other compounds or elements. Suitable biocompatible ceramic materials include, for example, magnesium aluminate ($MgO.Al_2O_3$), cordierite ($2MgO.2Al_2O_3.5SiO_2$), hydroxyapatite (i.e. $Ca_3(PO_4)_2$), etc.

Biocompatible macroporous ceramic particles 28 have an average diameter suitable for forming a suitable packed bed in cell-culture reactor 12 of the invention. In a preferred embodiment, biocompatible macroporous ceramic particles 28 have an average diameter in the range of from about five hundred microns up to about eight millimeters. In a particularly preferred embodiment, biocompatible macroporous ceramic particles 28 have an average diameter in the range of from about seven hundred microns up to about five millimeters.

Biocompatible macroporous ceramic particles 28 contain pores extending therethrough. "Macroporous particles," as that term is used herein, means the particles have pores of sufficient average pore diameter to allow culturing of cells within the pores and to allow transport to the cells by convective flow of medium through the pores of a significant portion of the oxygen and other nutrients consumed by the cells. Cells are disposed in the pores, for example, by attachment of the cells within the pores or by entrapment of cells. Surfaces of biocompatible macroporous ceramic particles 28 within the pores can be suitable for attachment of anchorage-dependent cells. In a preferred embodiment, the pores of biocompatible macroporous ceramic particles 28 have an average pore diameter which is significantly larger than the average cell diameter of cells cultured in packed bed 24. In one embodiment, the average pore diameter is in the range of from about five microns to about one hundred microns. In a particularly preferred embodiment, the average pore diameter is in the range of between about ten microns and about seventy microns.

Biocompatible macroporous ceramic particles 28 can be formed by a method suitable for forming biocompatible macroporous ceramic particles 28 suitable for use with the present invention. In a preferred embodiment of the invention, porous ceramic particles 28 are formed of magnesium aluminate ($MgO.Al_2O_3$). An example of a suitable method of forming suitable macroporous magnesium aluminate particles includes forming an aqueous solution of metal ions, such as by dissolving magnesium nitrate and aluminum nitrate in deionized water. An organic polyfunctional acid possessing at least one hydroxy and one carboxyl group, such as citric acid, is introduced to the metal ion solution. In a preferred embodiment, the molar ratio of the metal ions to citric acid is about 1:2. For example, a solution is formed by combining in a suitable vessel about thirty-six grams of magnesium nitrate and about one hundred and five grams of aluminum nitrate with about one hundred and seventy-seven grams of citric acid in about seven hundred milliliters of deionized water. The aqueous solution formed is then rapidly dehydrated at a temperature of about 70° C. in a revolving evaporator at a pressure of about thirty millimeters of mercury. Evaporation is terminated before the viscosity of the solution prevents removal of the solution from the vessel containing the solution (i.e. a few thousand centipoise at 70° C.). The partially dehydrated solution is then substantially dehydrated by exposing the solution to a temperature of about 85° C. at a pressure of a few millimeters of mercury for a period of time of about twenty-four hours in a vacuum oven. A solid foam results from dehydration. The solid foam comprises cells, the walls of which comprise a vitreous material. The solid foam is then heated rapidly to a temperature of about 1000° C. and is then calcined at 1000° C. for about five hours while exposed to air to thereby form suitable biocompatible macroporous magnesium aluminate particles.

In another preferred embodiment, suitable biocompatible macroporous cordierite particles are formed by forming a mixture of kaolin, talc, alumina, aluminum hydroxide and silica. The mixture is combined with water and methyl cellulose to form a slurry, which is then extruded under pressure through a die of suitable shape. The extruded slurry is then dried. After drying, the extruded material is fired for a period of several hours at temperatures in excess of 1000° C. to thereby form a cordierite. The cordierite is then reduced to particles of suitable size. The pore diameter of the cordierite is controlled by inclusion of talc particles in the cordierite. The cordierite particles are heated to a temperature of about 1400° C., thereby melting the talc and forming pores extending through the cordierite particles having a suitable average pore diameter.

In still another preferred method of forming suitable biocompatible macroporous ceramic particles, a hydroxyapatite, such as tricalcium phosphate powder, is mixed with naphthalene particles having a diameter of about five hundred microns. The mixture is compacted in a Reichle press and then heated in a suitable furnace, such as a Globar furnace, at a temperature of about 400° C. for about four hours to thereby sublimate and remove the naphthalene, thereby forming suitable pores in the hydroxyapatite. The porous hydroxyapatite is thereafter sintered for about eight hours at a temperature of about 100° C. and is then formed into biocompatible macroporous hydroxyapatite particles of suitable diameter.

In a preferred embodiment, the biocompatible macroporous ceramic particles 28 are generally spherical. However, it is to be understood that biocompatible macroporous ceramic particles can alternatively be configured in any shape suitable for forming packed bed 24 having interstitial passages extending therethrough. Examples of other suitable shapes include discs, flakes, beads, fibers, stars, rings, saddles, etc.

Medium 30 is recirculated through medium reservoir 32, whereby medium 30 is received into medium reservoir 32 from fresh medium source 34 through medium source supply conduit 36 and then returned to fresh medium source 34 through medium source return conduit 38. Medium 30 can be any fluid suitable for culturing cells. Many such media are known in the art. Examples of media suitable for culturing animal cells include: hormonally-defined media; serum-supplemented basal media, such as Dulbecco's Modified Eagle's Basal Medium; etc. Examples of culture media suitable for culturing microbes include well-defined media, undefined complex media, etc.

Nutrients are introduced to medium 30 at fresh medium source 34. It is to be understood, however, that oxygen and other nutrients can be dissolved in medium 30 at medium reservoir 32, at any suitable point in the path of flow of medium 30 between medium reservoir 32 and cell-culture reactor 12, at fresh medium source 34 or at cell culturing reactor 12. Suitable nutrients can be any nutrients suitable for culturing cells in the system and by the method of invention. Examples of suitable nutrients include, for example, yeast extract, amino acids, sugar, salt, vitamins, etc.

Medium 30 is sealed from the atmosphere at medium reservoir 32 by cover 33. Medium 30 is oxygenated, whereby oxygen is dissolved in medium 30 for transport to cells in packed bed 24. Sufficient oxygen is dissolved in medium 30 to culture cells in cell-culture reactor 12. In a preferred embodiment, medium 30 is oxygenated in medium reservoir 32 by surface aeration, whereby oxygen is directed from oxygen source 40 through oxygen conduit 42, which is formed of suitable tubing, such as glass, ceramic, stainless steel or other metal, polymers such as Teflon polytetrafluoroethylene, rubber, etc. Oxygen is directed through oxygen conduit 42 by a suitable method, such as by applying pressure to the oxygen at oxygen source 40. Medium 30 in medium reservoir 32 is agitated by a suitable means, such as by rotating agitator 44 within medium reservoir 32 either manually or by automated means, not shown, at a sufficient rate to suitably aerate medium 30.

In another embodiment, medium 30 can be oxygenated in medium reservoir 32 by sparging oxygen gas into medium reservoir 32 by a suitable sparging means, not shown. In still another embodiment, medium 30 can be oxygenated by a suitable membrane oxygenator, not shown, disposed at medium conduit 46. A suitable membrane oxygenator can include an oxygenator including a solid-phase oxygen gas-permeable membrane, such as suitable bundled hollow-fiber of a suitable material, such as polysulfone, or a suitable silicon tubing. Oxygen is conducted from an oxygen source to the membrane oxygenator. Oxygen is directed across the solid-phase membrane of the membrane oxygenator and contacts medium 30, thereby dissolving in medium 30 in an amount sufficient to culture cells in cell-culture reactor 12.

Medium 30, containing dissolved oxygen and other nutrients, is directed from medium reservoir 32 through medium conduit 46 to cell-culture reactor 12 by a suitable means. Medium conduit 46 is formed of a suitable tubing, such as glass, ceramic, stainless steel or other metal, polymers such as Teflon polytetrafluoroethylene, rubber, etc. Means for transporting medium 30 from medium reservoir 32 can include any suitable means for directing medium through medium conduit 46, such as pump 48 which is disposed at medium conduit 46. Pump 48 can be any suitable pump for directing medium 30 through medium conduit 46, such as a peristaltic pump. Pump 48 directs medium 30 from medium conduit 46 through inlet means 20 into inlet end 16 of cell-culture reactor 12.

Optionally, medium 30 can be oxygenated by directing oxygen from oxygen source 40 through oxygen conduit 50, which is formed of a suitable tubing, to medium 30 at inlet end 16 of cell-culture reactor 12. oxygen is introduced to medium 30 at inlet end 16 by a suitable means, such as by sparging, whereby oxygen gas is discharged from oxygen conduit 50 into medium 30 at inlet end 16 through oxygen inlet member 52. Oxygen inlet member 52 can be, for example, a suitable perforate tube or a suitable porous ceramic block. In another embodiment, oxygen is also conducted through oxygen conduit 54 and discharged through oxygen inlet member 56 within packed bed 24. Oxygen can also be discharged at a plurality of points within packed bed 24. For example, medium 30 can be oxygenated in packed bed 24 by a suitable solid-phase oxygen gas-permeable membrane, not shown, extending through packed bed 24. Examples of suitable solid-phase oxygen gas-permeable membranes include suitable silicon tubing, bundled hollow fiber formed of a suitable material, such as polysulfone, etc. Oxygen is conducted through the solid-phase membrane and at least partially dissolves in medium 30.

As another option, medium 30 can be treated to increase the solubility of oxygen in medium 30. For example, a suitable oxygen-carrier can be introduced to medium 30. An example of a suitable oxygen-carrier is perfluorocarbon. In one embodiment, medium 30 includes perfluorocarbon in the amount of about twenty percent by volume. The oxygen-carrier can be oxygenated prior to introduction of the oxygen-carrier to medium 30. The oxygen-carrier is then introduced as droplets to medium 30 which are directed through packed bed 24. Oxygen dissolved in medium 30 is transported from the perfluorocarbon and for consumption by the cell culture in packed bed 24. The perfluorocarbon is then directed out of packed bed 24 by medium 30 and separated from medium 30, for example, by employing a suitable liquid-liquid separator, not shown.

Packed bed 24 is suitably inoculated with a suitable cell culture to thereby establish a cell culture within packed bed 24. Suitable cell cultures for use with the invention include, for example, animal cells, such as mammalian cells, insect (Insecta or Hexapoda) cells and fish (Osteicthyes and Chondricthyes) cells. Mammalian cell types suitable for use with the present invention include cell types which have been adapted for growth in suspension cultures, such as HeLa (human), BHK (baby hampster kidney), L cells (mouse), hybridoma cells, etc. Mammalian cell types also suitable for use with the present invention include anchorage-dependent cell types such as 3T3 mouse fibroblasts, mouse bond marrow epithelial cells, murine leukemia virus-producing strains of mouse fibroblasts, primary and secondary chick fibroblasts, WI-38 human fibroblast cells, normal human embryo lung fibroblast cells (HEL299, ATCC #CCL137), etc. Cells which are particularly suitable for use with the present invention include Chinese hampster ovary (CHO) cells that grow in suspension or are anchorage dependent and have been transformed with functioning vectors carrying foreign genes, and transformed rat pituitary cells, AtT20, which have been transfected with human proinsulin gene using SV-40 viral promoter.

In a preferred embodiment, a significant portion of the cells of the cell culture are disposed within pores of biocompatible macroporous ceramic particles 28 of packed bed 24. Medium 30 is directed from inlet 20 into packed bed 24 within cell-culture reactor 12 for delivery of oxygen and other nutrients to the cell culture within packed bed 24. Flow of medium 30 from inlet 20 to outlet 22 can be upward, downward or horizontal. When medium 30 is oxygenated by sparging through inlet member 52, flow of medium 30 through cell culturing reactor 12 is in an upward direction.

Dissolved oxygen and other nutrients in medium 30 are transported by convection of medium through the pores of biocompatible macroporous ceramic particles 28 to cells disposed within the pores, where at least a portion of the dissolved oxygen and other nutrients are consumed by the cells. At least a portion of the medium within cell-culture reactor 12 is directed through the pores at a rate and in an amount sufficient to provide by convective flow of the medium through the pores a sufficient portion of the oxygen and other nutrients consumed by the cells to maintain the viability of the cell culture. Cell waste and cell product are released by the cells into medium 30 within the pores. Cell waste and cell product in medium 30 are transported by medium 30 from the packed bed 24 to outlet end 18 of the cell-culture reactor 12 and through outlet 22 to medium conduit 57 for discharge from cell-culture reactor 12.

Medium 30 is then directed through medium conduit 57 to gas-liquid separator 58 to remove undissolved sparged oxygen. Medium 30 is then directed from gas-liquid separator 58 through medium conduit 59 to recovery means 60 for separation of cell product from medium 30. An example of a suitable recovery means 60 is a suitable chromatographic column for recovery of cell product. Medium 30 from which cell product has been recovered is then directed from recovery means 60 through medium conduit 62 to waste treatment means 64 for treatment of medium 30 to remove cell waste released by cells in packed bed 24. An example of a suitable waste treatment means 64 is a suitable filter for separation of cell waste from medium 30. Medium 30 is then directed through medium conduit 66 to medium reservoir 32. Additional nutrients can be directed from fresh medium source 34 through fresh medium conduit 36 into medium 30 at medium reservoir 32. In another embodiment, medium 30 can be treated at medium reservoir 32 for recovery of cell product and removal of cell waste. Means for passing medium 30 through packed bed 24 includes, for example, medium reservoir 32, pump 48 and cell-culture reactor 12.

It is to be understood that any kind of cell-culture reactor which is suitable for flowing a medium through a packed bed of suitable biocompatible macroporous ceramic particles can be employed to culture cells by the method of the present invention. Reactors can be used where the packed bed, the medium, or both the packed bed and the medium are in motion. Examples of other suitable cell-culture reactors include airlift reactors, Carberry-type reactors, loop reactors, etc.

Figure 2:
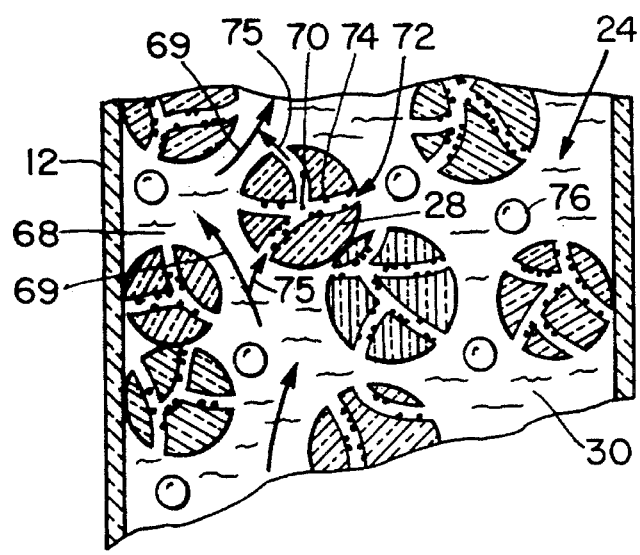
FIG. 2 is a section view in-part of a packed bed of a cell-culture reactor of one embodiment of the invention.

As shown in FIG. 2, packed bed 24 includes interstitial passage 68 defined by biocompatible macroporous ceramic particles 28. Oxygen and nutrients dissolved in medium 30 are directed by interstitial flow 69 of medium 30 through interstitial passage 68 to pores 70 extending through biocompatible macroporous ceramic particles 28. Pores 70 extend through biocompatible macroporous ceramic particles 28 and can form converging and diverging pathways through biocompatible macroporous ceramic particles 28.

Cell culture 72 is formed of cells 74 disposed within pores 70. Cells 74 within pores 70 can be anchorage-dependent cells which are attached to biocompatible macroporous ceramic particles 28. Alternatively, cells 74 can be suspension cells which do not need to be attached to a substrate. Suspension cells can be entrapped within pores 70.

A portion of interstitial flow 69, containing dissolved oxygen and other nutrients, separates from medium flow 69 through interstitial passage 68 to form convective flow 75 of medium 30 through pores 70 of biocompatible macroporous ceramic particles 28. The rate and amount of convective flow 75 is sufficient to provide by convective flow 75 of medium 30 through pores 70 a sufficient portion of the oxygen and other nutrients consumed by cells 74 to maintain the viability of the cell culture. In a preferred embodiment, a predominant portion of the oxygen and other nutrients are provided to cell culture 72 by convective transport in convective flow 75 through pores 70. In a particularly preferred embodiment, a substantial portion of the oxygen and other nutrients required for cell culturing of cells 74 are provided by convective transport in convective flow 75.

"Cell-culturing," as that term is used herein, means culturing cells by a method which includes controlling the cell density of a cell culture, controlling the cell activity of a cell culture, or controlling both the cell density of a cell culture and the cell activity of the cell culture. "Cell activity," as that term is used herein, means production rate by cells of cell products such as, for example, viruses, proteins expressed by recombinant DNA molecules within the cells, natural proteins, nucleic acids, etc.

The average diameter of interstitial passage 68 is determined by the size and shape of biocompatible macroporous ceramic particles 28. The relative average diameters of interstitial passage 68 and of pores 70 is sufficient to protect cells 74 from shearing stresses of interstitial flow 69. The average pore diameter of porous ceramic particles 28 is sufficient to allow control of cell density of cell culture 70 in packed bed 24 by controlling convective transport of oxygen and other nutrients within pores 70 to cells 74. The rate of convective transport of oxygen within pores 70 can be controlled by controlling the rate of flow of medium 30 through packed bed 24. Cell density of cell culture 72 in packed bed 24 can be proportionately related to the flow rate of medium 30 through packed bed 24 as generally represented by the equation:

(Cell Density)=K(Flow Rate)

where K is a constant.

Oxygen and other nutrients dissolved in medium 30 at cells 74 which have been transported by convection from interstitial passage 68 in convective flow 75 are at least partially consumed by cells 74. Cells 74 are thereby cultured within pores 70 of biocompatible macroporous ceramic particles 28 within cell-culture reactor 12. In one embodiment, bubbles 76 of oxygen gas are formed in cell-culture reactor 12 by sparging oxygen gas into cell-culture reactor 12. A substantial portion of bubbles 76 have a diameter which is larger than the average pore diameter of pores 70 and do not penetrate pores 70. Bubbles 76 are directed through interstitial passage 66 of packed bed 24. Cells 74 in pores 70 are protected form shear stresses caused by interstitial flow 69. Cells 74 are also protected from agitation by bubbles 76. Bubbles 76 can dissolve in medium 30 as dissolved oxygen, which is transported by convective flow 75 and diffusion to cells 74 in pores 70 where it is consumed.

Cell product and cell waste generated by cells 74 is transported from cells 74 by convective flow 75 of medium 30 out of pores 70. Convective flow 75, containing cell product and cell waste, is directed out of pores 70 and combines with interstitial flow 69 in interstitial passage 68.

The length of packed bed 24 and the rate of convective transport of oxygen and other nutrients can be optimized for a selected cell line in accordance with, for example, the solubility of oxygen in medium 30, the rate of introduction of gaseous oxygen into packed bed 24, the average diameter of interstitial passage 68, the average pore size of biocompatible macroporous ceramic particles 28, the relative average diameter of interstitial passage 68 and pores 70, the rate of flow of medium 30 through cell-culture reactor 12 and the optimum cell density for the cell line chosen for culturing in cell-culture reactor 12.

Figure 3:
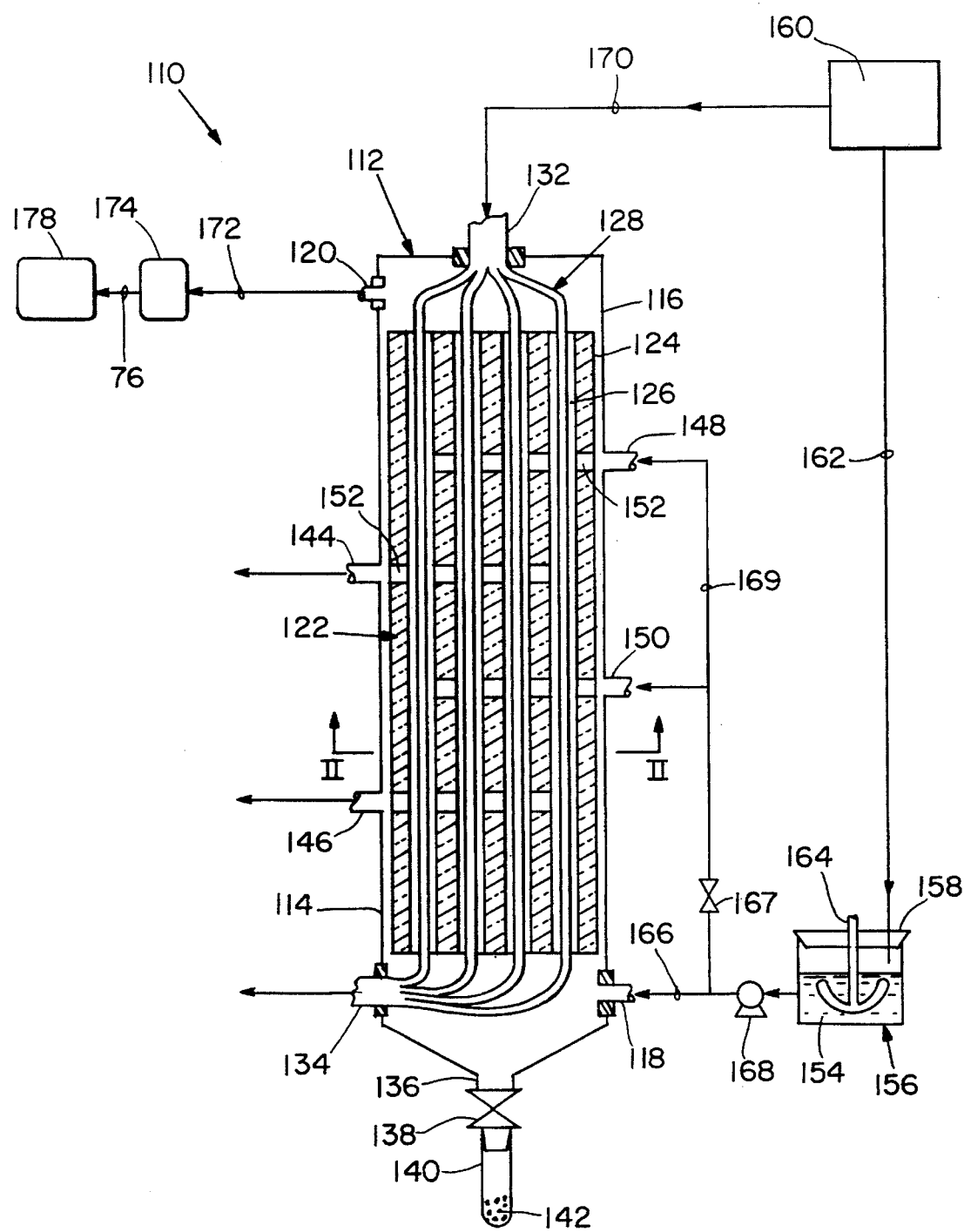
FIG. 3 is a schematic illustration of one embodiment of a cell-culturing system of the invention.

In an alternate embodiment of the present invention, shown in FIG. 3, cell-culture system 110 includes cell culture reactor 112. Cell-culture reactor 112 has a bottom end 114 and a top end 116. Cell-culture medium inlet 118 is disposed at bottom end 114 of cell-culture reactor 112 for conducting a suitable medium into cell-culture reactor 112. Medium outlet 120 is disposed at top end 116 of reactor 112 for directing spent medium out of reactor 112.

Biocompatible macroporous support 122 is disposed within reactor 112 between medium inlet 118 and medium outlet 120. Biocompatible macroporous support 122 includes biocompatible macroporous walls 124 which intersect to define passages 126. Passages 126 in reactor 112 provide fluid communication between medium inlet 118 and medium outlet 120.

Cells are disposed in the pores of the biocompatible macroporous support 122, for example, by attachment of the cells within the pores or by entrapment of the cells. Surfaces of biocompatible macroporous support 122 within the pores can be suitable for attachment of anchorage-dependent cells. In a preferred embodiment, the pores of biocompatible macroporous support 122 have a pore diameter which is significantly larger than the average cell diameter of cells cultured in reactor 112. In one embodiment, the average pore diameter is in the range of between about five microns and two hundred microns. Preferably, the average pore diameter is in the range of between about ten microns and about seventy microns.

Oxygen-permeable tubes 128 are disposed within passages 126 and provide fluid communication between oxygen-containing-gas inlet 132 at top end 116 of reactor 112 and oxygen-containing-gas outlet 134 at bottom end 114. Oxygen-permeable tubes 128 are comprised of a material which is sufficiently permeable to oxygen and the tube walls of oxygen-permeable tubes 128 are sufficiently thin to allow oxygen to migrate from oxygen-containing-gas within oxygen-permeable tubes 128 across the oxygen-permeable tube walls to a suitable medium at a rate sufficient to culture cells disposed within pores of biocompatible macroporous support 122. Preferably, oxygen-permeable tube 128 is substantially liquid-impermeable. An example of a suitable oxygen-permeable tubing is Siliastic silicon medical grade tubing, commercially available from Dow Corning Corporation.

Sample port 136 is disposed at bottom end 114 and includes sample port valve 138. Sample tube 140 is fitted at sample port valve 138. Sample tube 140 can be formed of the same material as reactor 112. Preferably, reactor 112 is disposed vertically, such that bottom end 114 of cell-culture reactor 112 is lower than top end 116. Suspension cells 142 dislodged from biocompatible macroporous support 122 by turbulence or by cell growth can settle by gravitational force within reactor 112 and pass through sample port valve 138 into sample tube 140 for collection therein. Alternatively, reactor 112 can be disposed substantially horizontally. If reactor 112 is disposed substantially horizontally, bottom end 114 and top end 116 would be a first end and second end, respectively.

Intermediate outlet ports 144,146 are disposed at reactor 112 between medium inlet 118 and medium outlet 120 for withdrawing spent medium from within reactor 112. Spent medium withdrawn from reactor 112 can be analyzed for monitoring the system conditions of cell-culture system 110 and for controlling conditions, such as pH, within medium as it is conducted through passages 126 within reactor 112. Intermediate inlet ports 148,150 are disposed between medium inlet 118 and medium outlet 120 for directing fresh medium into cell-culture reactor 112. Alternatively, the spent medium withdrawn from cell-culture reactor 112 through intermediate ports 144,146 can be treated such as by introducing additional nutrients to the spent medium and then returned to rector 112 through intermediate inlet ports 148, 150. The dimensions of reactor 112 can, therefore, be independent of the solubility of nutrients in medium 140 or the concentration of nutrients, other than oxygen, in medium at inlet end 114 of reactor 112.

Biocompatible macroporous support 122 can define openings 152 proximate to intermediate outlet ports 144,146 and intermediate inlet ports 148,150 for allowing sampling of medium from various passages 126. Sampling of medium within reactor 112 can be accomplished by conventional or unconventional means. Examples of conventional means of sampling reactor 112 include, for example, introduction of a syringe needle through intermediate outlet ports 144,146 or by draining medium from intermediate outlet ports 144,146. Medium can be directed into reactor 112 through intermediate inlet ports 148,150, such as by application of pressure to a medium source in fluid communication with intermediate inlets 148,150.

In one illustration of the method of the invention, medium 154 is directed from fresh medium source 156 through medium inlet 118 into reactor 112. Medium 154 can include nutrients, other than oxygen, in an amount sufficient to culture cells in reactor 112.

Medium 154 can be any fluid suitable for culturing cells including nutrients suitable for culturing the desired cell culture. Many such media are known in the art, such as those described as being suitable for the embodiment of the invention shown in FIGS. 1 and 2.

Medium 154 is sealed from the atmosphere at fresh medium source 156 by cover 158. Optionally, medium 154 can be oxygenated at fresh medium source 156, whereby oxygen is dissolved in medium 154 at fresh medium source 156 for transport to cells at biocompatible macroporous support 122. However, it is to be understood that oxygen does not need to be introduced to medium 154 at fresh medium source 156 on or before introduction of medium 154 to reactor 112. In a preferred embodiment, medium 154 is oxygenated in fresh medium source 156 by surface aeration whereby oxygen is directed from oxygen source 160 through oxygen conduit 162, An example of a suitable oxygen-containing gas is air. Oxygen-containing gas is directed through oxygen conduit 162 by a suitable method, such as applying pressure to the oxygen at oxygen source 160. Medium 154 in fresh medium source 156 is agitated by a suitable means, such as by rotating agitator 164 within fresh medium source 156 either manually or by automated means, not shown, at a sufficient rate to suitably aerate medium 154.

In another embodiment, medium 154 can be oxygenated in fresh medium source 156 by a suitable sparging means, not shown. In still another illustration, medium 154 can be oxygenated by a suitable membrane oxygenator, not shown, disposed at medium conduit 166. A suitable membrane oxygenator can include, for example, an oxygenator including a solid-phase oxygen gas-permeable membrane, such as a suitable bundled hollow fiber formed of a suitable material, etc. Examples of suitable materials include polysulfone, suitable silicone tubing, etc. Oxygen is conducted from an oxygen source to the membrane oxygenator. Oxygen is directed across the solid-phase membrane of the membrane oxygenator and contacts medium 154, thereby dissolving in medium 154.

Medium 154, containing dissolved oxygen and other nutrients, is pumped by pump 168 from fresh medium source 156 through medium conduit 166 to reactor 112 by a suitable means. Means for transporting medium 154 from fresh medium source 156 can include any suitable means for directing medium through medium conduit 166, such as pump 168 which is disposed at medium conduit 166. Pump 168 can be any suitable pump for directing medium 154 through medium conduit 166, such as a peristaltic pump. Pump 168 directs medium 154 from medium conduit 166 through medium inlet 118 into bottom end 114 of cell-culture reactor 112 at a rate sufficient to support a cell culture disposed within pores of biocompatible macroporous support 112. Optionally, valve 167 can be opened to direct medium 154 from fresh medium source 156 through medium conduit 169 and through intermediate inlet ports 148,150.

Biocompatible macroporous support 122 is inoculated with cells to establish a cell culture within biocompatible macroporous support 122. Cell culture system 110 can be used to culture a wide variety of cells, including, for example, the cells identified as being suitable for the embodiment of the invention shown in FIGS. 1 and 2. A significant portion of the cells of the culture are disposed within pores of biocompatible macroporous support 122. Medium 154 is directed through medium inlet 118 into passages 126 within biocompatible macroporous support 122 for delivery of oxygen and other nutrients to the cell culture within biocompatible macroporous support 122.

Dissolved oxygen and other nutrients in medium 154 migrate in medium 154 from passages 126 into the pores of biocompatible macroporous support 122 and are delivered to cells disposed within the pores, where at least a portion of the dissolved oxygen and other nutrients are consumed by the cells. Cell waste-products and cell-products are released by the cells into medium 154 within the pores. The cell waste-products and cell-products migrate through medium 154 out of the pores and into passages 126 for delivery with medium 154 out of reactor 112.

Oxygen-containing gas is directed from oxygen-containing gas source 160 through oxygen-containing-gas conduit 170 to oxygen-containing-gas inlet 132. Oxygen-containing gas is delivered from oxygen-containing-gas source 160 by a suitable means, such as by pressurizing oxygen-containing gas at oxygen-containing-gas source 160.

Oxygen-containing gas is delivered through oxygen-containing-gas inlet 132 and into oxygen-permeable tubes 128. Oxygen migrates from within oxygen-permeable tubes 128 across the oxygen-permeable tube wall to medium 154 which is being conducted through passages 126 of biocompatible macroporous support 122. The rate of flow of oxygen-containing gas from oxygen-containing-gas source 160 through oxygen-permeable tubes 128 is sufficient to allow oxygen within oxygen-containing gas to migrate across the oxygen-permeable tube wall at a rate sufficient to maintain a concentration of dissolved oxygen within medium 154 which will sustain the cell culture within reactor 112. Oxygen migrating across the oxygen-permeable tube wall dissolves in medium 154 and is consumed by cells of the culture. Oxygen which is dissolved in medium 154 following migration across the oxygen-permeable tube wall migrates within medium 154 from the oxygen-permeable tube wall to cells within pores of biocompatible macroporous support 122. Oxygen is dissolved in medium 154 from oxygen-permeable tube 128 along passages 126 as oxygen previously dissolved in medium 154 is consumed by the cell culture within cell-culture reactor 112. The concentration of dissolved oxygen in medium 154 within reactor 112 is thereby maintained throughout the path of flow of medium 154 within passages 126 at a level which will sustain the cell culture disposed within biocompatible macroporous support 122.

Cells which have become dislodged from the pores can settle within reactor 112 by gravity. The rate of flow of medium 154 through passages 126 can be, always, or at select time intervals, at a velocity which is sufficiently slow to allow cells to settle within reactor 112 against the direction of flow of medium 154. Settling cells can thereby pass through sample port 136 and collect in sample tube 140 at bottom end 114. Cells collected within sample tube 140 can be removed from cell-culture system 110 by closing sample port valve 138 and removing sample tube 140 from cell-culture system 110. Collected cells 142 in sample tube 140 can be removed from cell-culture system 110 without interruption of flow of medium 154 through cell-culture reactor 112 or operation of cell-culture system 110.

Oxygen-containing gas within oxygen-permeable tubes 128 which does not migrate across the oxygen-permeable tube wall is conducted out of oxygen-permeable tube 128 through oxygen-containing-gas outlet 134 at bottom end 114 of reactor 112. Oxygen-containing gas exiting reactor 112 can be treated for return to oxygen-containing-gas source 160, such as by introducing additional oxygen gas to oxygen-containing gas. The direction of flow of oxygen-containing gas within oxygen-permeable tubes 128 is shown in FIG. 3 as being countercurrent to the direction of flow of medium 154 within passages 126. However, the direction of flow of oxygen-containing gas within oxygen-permeable tubes 128 does not substantially affect the productivity of the cell culture. It is to be understood that the oxygen-containing gas and medium 154 can flow concurrently, in a cross-flow arrangement with respect to one another, or in any other suitable configuration within cell-culture reactor 112.

Spent medium 154, containing cell-products and cell waste-products, is conducted through medium outlet 120. Spent medium 154 can also be withdrawn from reactor 112 at intermediate medium outlet ports 144,146 for analysis or for treatment for return to fresh medium source 156. Medium 154 is directed through medium outlet 120 and then through conduit 172 to recovery means 174 for separation from medium 154 of cell-products formed in reactor 112. An example of a suitable recovery means 174 is a suitable chromatographic column for recovery of cell-products. Medium 154 from which cell product has been recovered is then directed from recovery means 174 through medium conduit 176 to waste-treatment means 178 for treatment of medium 154 to remove cell waste-products released by cells in biocompatible macroporous support 122. An example of suitable waste-treatment means 178 is a suitable filter for separation of cell waste-products from medium 154.

It is to be understood that, although a suitable productivity and concentration of cell product can be obtained in medium 154 by directing medium 154 from fresh medium source 156 through reactor 112 and from reactor 112 to recovery means 178 without recycle of medium 154, medium 154 can be recycled following treatment in waste-treatment means 178 to fresh medium source 156 for recirculation through reactor 112. It is also to be understood that any kind of reactor which is suitable for flowing a medium through a biocompatible macroporous support 122 can be employed to culture cells by the method of the present invention. Reactors may be used where the biocompatible macroporous supports, the medium, or both the biocompatible macroporous support and the medium are in motion.

Medium conduits and an oxygen-containing-gas conduit can be formed of a suitable material, such as: glass; ceramic; stainless steel or other metal; polymers, such as Teflon polytetrafluoroethylene; rubber; etc. Reactor 112 can be formed of a suitable material, such as glass, steel, etc.

Figure 4:
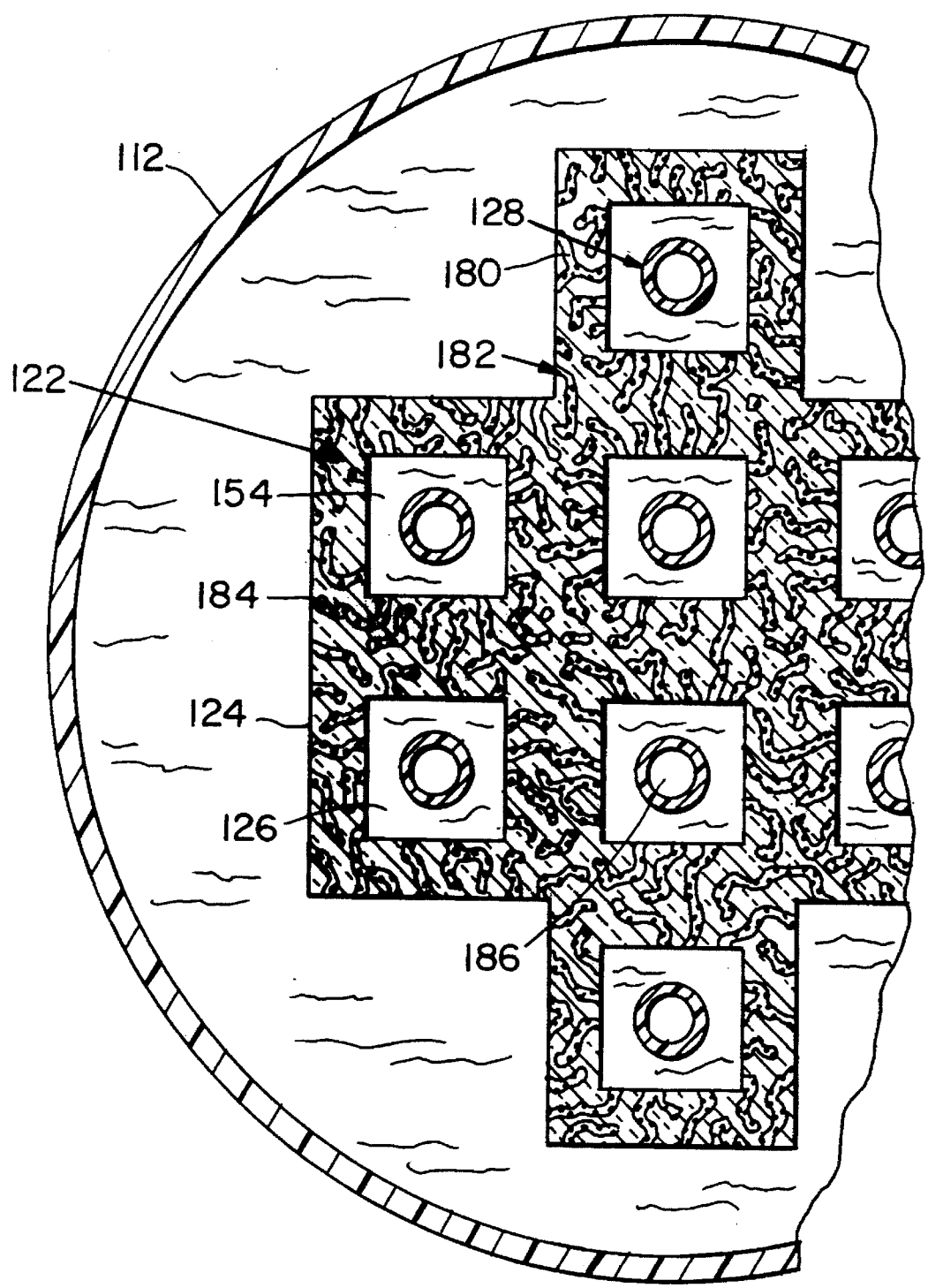
FIG. 4 is a broken-away section view, taken along line IV—IV of FIG. 3, of one embodiment of the cell-culture reactor of the invention.

AS shown in FIG. 4, biocompatible macroporous support 122 is disposed within reactor 112 and includes passages 126 defined by biocompatible macroporous walls 124. Oxygen-permeable tubes 128 are disposed within passages 126. Pores 180 extend within biocompatible macroporous walls 124. Pores 180 can extend through biocompatible macroporous walls 124 and can form converging and diverging pathways through biocompatible macroporous walls 124. Cell culture 182 is formed of cells 184 disposed within pores 180. Cells 184 within pores 180 can be anchorage-dependent cells which are attached to biocompatible macroporous walls 124. Alternatively, cells 184 can be suspension cells which do not need to be attached to a substrate. Suspension cells can be entrapped within pores 180.

At least a portion of oxygen within oxygen-containing gas 186 conducted through oxygen permeable tubes 128 migrates across oxygen-permeable tube walls of oxygen-permeable tubes 128 to medium 154 which is being conducted through passages 126. Oxygen which has migrated across the oxygen-permeable tube walls dissolves within medium 154. Dissolved oxygen and other nutrients within medium 154 migrate from passages 126 into pores 180 by diffusion or by convection of medium 154 within passages 126. Dissolved oxygen and other nutrients at pores 180 diffuse into pores 180 to cells 184 of cell culture 182. The dissolved oxygen and other nutrients are at least partially consumed by cells 184 which consequently generate cell-products and cell waste-products. The cell-products and cell waste-products are dissolved in medium 154 and diffuse within medium 154 out of pores 180 and into passages 126. Medium 154 within passages 126 conduct cell-products and cell waste-products through passages 126 and out of cell-culture reactor 112. As oxygen is depleted from medium 54 by cells 184, additional oxygen from oxygen-containing gas and oxygen-permeable tubes 128 migrates across the oxygen-permeable tube wall to medium 154 and is dissolved therein for continued consumption of oxygen by cells 184.

The invention will now be further and specifically described by the following examples. All parts and percentages are by weight unless otherwise stated.

EXAMPLE 1

Biocompatible macroporous ceramic particles having diameters in the range of between about 589 micrometers and 850 micrometers were disposed in a cell-culture reactor to form a packed bed having a diameter of 2.2 cm and a height of one centimeter. The cell-culture reactor was inoculated with a culture of anchorage-dependent animal cells. The cell line was of transformed rat pituitary cells, AtT20, which were transfected with human proinsulin gene using SV-40 viral promoter. A culture medium was prepared by supplementing Dulbecco's Modified Eagles's basal medium to 10% with fetal bovine serum. AtT20 secretes human proinsulin constitutively at the rate of 1–2 $\mu$U/hr per $10^5$ cells. A medium reservoir was continually perfused with fresh medium and the perfusion rate was adjusted so that the glucose and the lactate concentrations in the medium reservoir were maintained in the range of between about fourteen and twenty millimoles and between about fifteen and twenty-one millimoles, respectively. The medium in the medium reservoir was oxygenated by surface aeration with continuously supplied fresh air which had been sterilized by filter. The aerated medium was circulated through the cell-culture reactor using a peristaltic pump.

Figure 5:
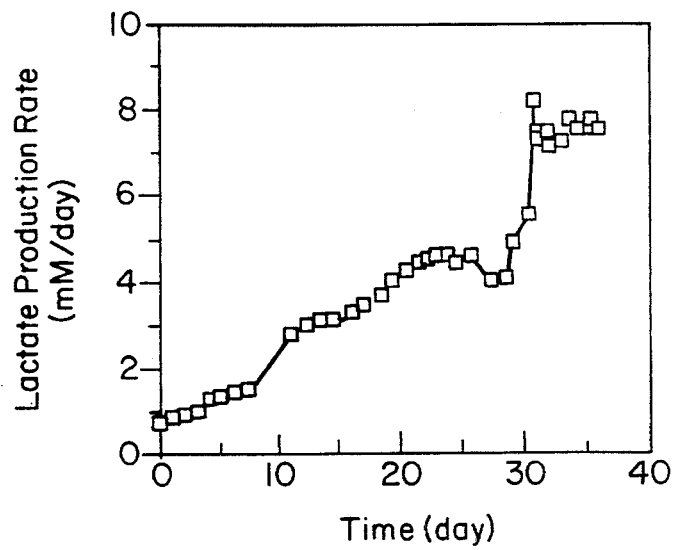
FIG. 5 is a plot of lactate production rate of transformed rat pituitary cell, AtT20, which was transfected with human proinsulin gene using SV-40 viral promoter and inoculated into the cell-culture reactor illustrated in FIG. 1.
Figure 6:
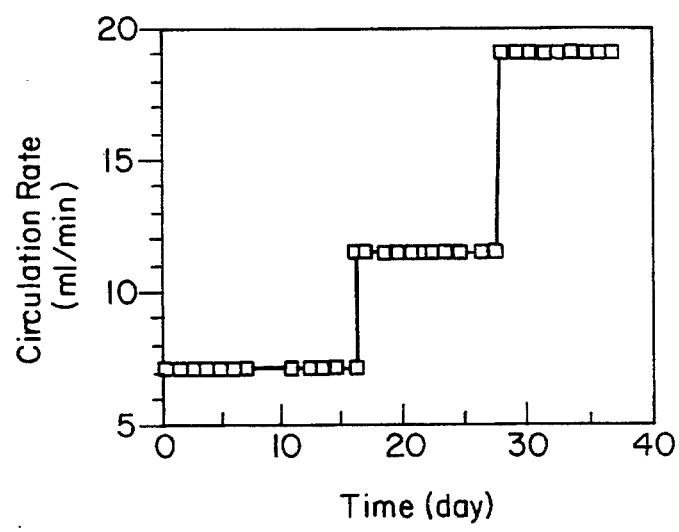
FIG. 6 is a plot of circulation rate in milliliters per minute of medium through the AtT20 cell culture for which lactate production rate was plotted in FIG. 5 and employing the cell-culture system illustrated in FIG. 1.
Figure 7:
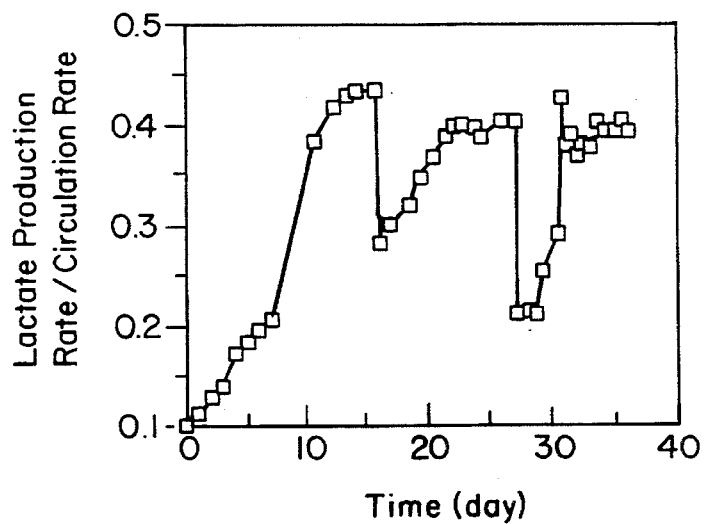
FIG. 7 is a plot of the ratio of lactate production rate by the AtT20 cell culture in the cell-culture reactor to the circulation rate of medium through the cell-culture system illustrated in FIG. 1 over the same period of time illustrated in FIGS. 5 and 6.

Lactate production rate of the cell culture in millimoles per day is plotted in FIG. 5. The circulation of medium through the cell-culture reactor is plotted in FIG. 6. As can be seen in FIGS. 5 and 6, cell activity, measured in terms of lactate production rate, reached a plateau several days after each increase in circulation rate of medium through the cell-culture reactor. FIG. 7 is a plot of the ratio of lactate production rate to circulation rate through the cell-culture reactor. As can be seen in FIG. 7, each time the circulation rate is increased, the ratio of lactate production rate to circulation rate decreases and then returns to the previous constant value.

Figure 8:
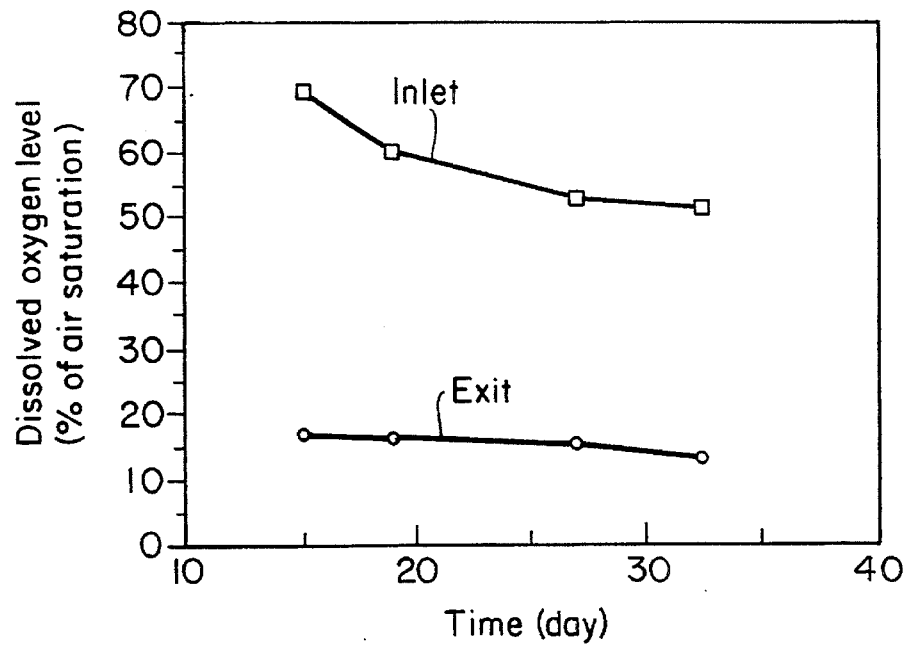
FIG. 8 is a plot of dissolved oxygen, as a percentage of oxygen saturation of the medium, in medium entering and leaving the packed bed which was inoculated with transformed rat pituitary AtT20 cell culture from day 15 through day 33 of the period of time illustrated in FIGS. 5, 6 and 7.
Figure 9:
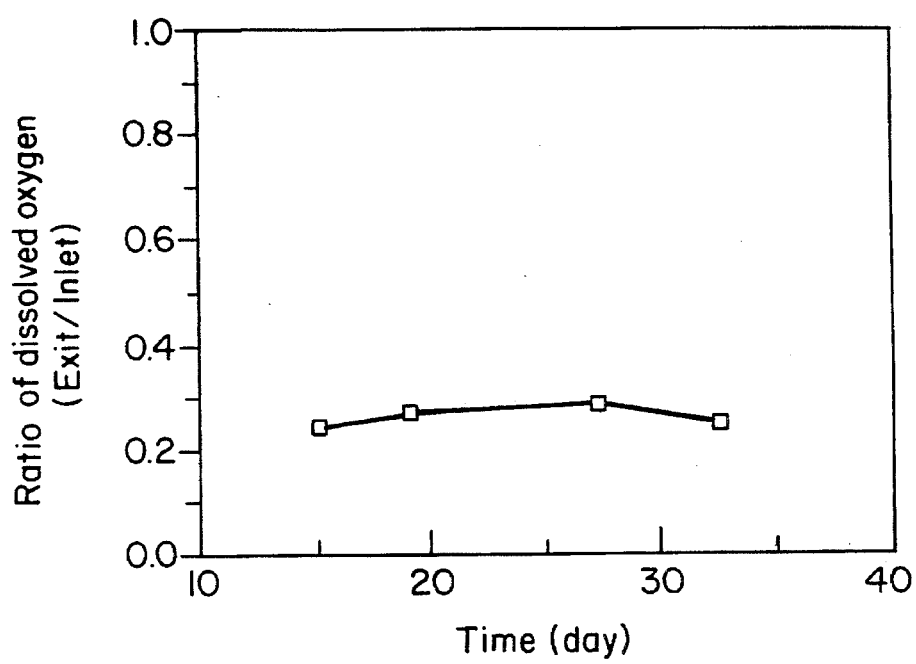
FIG. 9 is a plot of the ratio of dissolved oxygen in medium existing the cell-culture reactor to the dissolved oxygen in medium entering the AtT20 cell culture over the same period of time illustrated in FIG. 8.

FIG. 8 is a plot of dissolved oxygen content as a percent of saturation at an inlet end and an outlet end of the cell-culture reactor over a period of time from the fifteenth day to the thirty-third day of the reaction period illustrated in FIG. 5 through FIG. 7. FIG. 9 is a plot of the ratio of dissolved oxygen as a percent of saturation at the outlet end to dissolved oxygen at the inlet end over the same period of time plotted in FIG. 8. As can be seen in FIGS. 8 and 9, the ratio of dissolved oxygen remains at an approximately constant level despite incremental increases in the circulation rate of medium through the cell-culture reactor. Therefore, the rate of convection through the pores in the biocompatible macroporous ceramic particles controlled lactate production in the cell-culture reactor. Lactate production rate, and, therefore, cell density, increased proportionately with the circulation rate of medium through the cell-culture reactor because the rate of convection through the pores of the biocompatible macroporous ceramic particles varied proportionately with the rate of medium flow through the cell-culture reactor.

Based on the specific lactate production of AtT20, the total number of viable cells in the cell culturing reactor was estimated to be about $1.94 \times 10^9$. Cell density within the cell-culture reactor was therefore calculated to be $5.1 \times 10^8$ cells/cm$^3$. The beads were then withdrawn from the packed bed and subjected to DNA assay. DNA assay indicated that the packed bed contained $2.6 \times 10^9$ cells. Insulin activity of the product stream was determined by radioimmuno assay. The total insulin production rate was estimated to be 0.017 units per hour at the end of reactor operation. Using the estimated viable cell number based on the lactate production, the specific insulin productivity was calculated to be 0.88 µU/hr per $10^5$ cells.

EXAMPLE 2

A. Cell line and Stock Culture Maintenance

Bioreactor experiments were conducted with ATCC-CRL-1606 (American Type Culture Collection, Rockville, Md.), a murine-murine hybridoma cell-line, producing anti-(human fibronectin) IgG monoclonal antibody (Schoen et al., Hybridoma, 1:99 (1982)). CRL-1606 is strictly a suspension cell line: it exhibits no tendency to clump to other cells or to surfaces of T-flasks. This cell line was propagated in: Iscove's Modified Dulbecco's Medium (hereinafter "IMDM"), commercially available from Sigma Chemical Co.) supplemented with 5% (v/v) fetal bovine serum (hereinafter "FBS"), commercially available from Sigma Chemical Co.; 10 units/mL penicillin, commercially available from Sigma Chemical Co.; and 10 µg/mL streptomycin (Sigma Chemical). The cell-line was maintained at 37° C. in an air environment and were diluted five- to ten-fold every two or three days. Cell viability was maintained at greater than 95%, and only cells that had been maintained in an exponential growth phase for less than one month were used.

B. Single-Pass Bioreactor Construction

A macroporous cordierite monolith, 200 channels/square inch and four inches long, was obtained from Corning Glass Works. The monolith was wetted and sliced into five cylinders, 0.97 cm in diameter, with a spatula. Rough edges were ground down and polished. Nominal ceramic porosity was 50% with a mean pore size of 20–22 µm. Nominal pore size distribution ranged from less than 2 µm to more than 150 µm in diameter.

The monoliths were immersed in a boiling 10% nitric acid solution for one hour to leach out any heavy metal ions and other toxic impurities possibly introduced by the manufacturing process. This was followed by extensive rinsing in deionized water and phosphate-buffered saline (hereinafter "PBS") solution at room temperature. The monoliths were dried overnight at 60° C. in a vacuum oven, commercially available from VWR Scientific, and the total dry ceramic mass measured. The monoliths were aligned end-to-end and inserted into a glass tube, 1.0 cm by 50 cm, one at a time.

Silastic medical-grade silicone tubing, commercially available from Dow Corning Corp., 0.094 cm in diameter, was threaded through each square channel for a total of 21 tubes running the length of the bioreactor. At each end of the glass tube, the silicone tubes were gathered, threaded through a hole in the side of a silicone rubber stopper and epoxied into a short glass tube with T674 epoxy, commercially available from Amicon Division, W. R. Grace Co. All glass tubes were attached to the rubber stoppers using RVT-106 silicone rubber sealant, commercially available from General Electric Company to complete the bioreactor construction.

Since the hybridoma cell line used in these experiments is a suspension cell line, cells growing in the pores of the ceramic can also slough off into the flowing medium stream and be swept out of the monolith. In a laboratory-scale bioreactor, however, the superficial liquid velocity may not always be high enough to carry all cells out of the reactor. A short glass tube, 1.0 cm by 5 cm, was added at the base of the monolith to retain cells that had settled against the upward liquid flow. Cells collected in this tube were bled from the system as needed.

The medium feed line was connected to a central medium feed bottle containing IMDM which was supplemented with 5% (v/v) FBS, 10 units/mL penicillin, and 10 µg/mL streptomycin, all commercially available from Sigma Chemical Co. Feed medium was maintained at 4° C. throughout the experiment, but was warmed to 37° C. by the time it entered the base of the single-pass bioreactor. The same medium feed bottle supplied both the single-pass and recycle bioreactors for an accurate side-by-side comparison for reactor performance.

C. Recycle Bioreactor Construction

The same cordierite monolith described above was wetted and sliced into a single cylinder, 2.4 cm in diameter, with a spatula. The cylinder was immersed in boiling 10% nitric acid solution for the same duration as the single-pass bioreactor monoliths. After rinsing in deionized water and PBS solution, the wet monolith was inserted into a glass tube, 2.5 by 10 cm, and excess ceramic chips were flushed from the monolith with deionized water. The monolith was dried overnight at 60° C. in a vacuum oven, commercially available from VWR Scientific. The dry mass was determined as the mass difference between the dry monolith and glass tube and the glass tube alone. Glass funnels were then attached to both ends of the tube using RTV-106 silicone rubber sealant.

A 250 ml microcarrier spinner flask, commercially available from Bellco Glass, Inc. served as a central medium reservoir for the recycle bioreactor, from which medium was pumped through Norprene tubing, commercially available from Cole-Parmer Instrument Co., and a peristaltic pump, also commercially available from Cole-Parmer Instrument Co., into the base of the monolith. Medium flowed upward through square channels in the monolith and returned to the reservoir through silicone tubing, commercially available from Cole-Parmer Instrument Co. Recirculation ports into the reservoir were constructed from 0.25 inch stainless steel tubing. Feed and product stream ports were constructed from 0.0625 inch stainless steel tubing. Fresh medium was provided to the reservoir from a common medium feed bottle that fed the same medium to both bioreactors. Surface agitation in the reservoir was provided by the impellor to facilitate oxygen mass transfer into the reservoir. Spinner agitation rate and recirculation pump head rotational speed were measured with a Pioneer Model DS303 stroboscope, commercially available from Cole-Parmer Instrument Co.

D. Inoculation Procedure

Both bioreactors were inoculated with CRL-1606 hybridoma cells using a modification of a procedure previously described in Bognar et al., *J. Tissue Culture Methods*, 8:147 (1983). A large volume of stock culture was centrifuged at 200 times the force of gravity for ten minutes and most of the supernatant was aspirated off. The cells were then diluted in spent medium to achieve a final concentration of about $10^7$ cells/mL. This concentrated cell suspension was added to the central medium reservoir of the recycle bioreactor and to the medium feed of the single-pass bioreactor. The cell suspensions were pumped through the ceramic monoliths until clear evidence was obtained that the suspensions filled both reactors. Pumps were then turned off and the monoliths oriented horizontally. Cells were allowed to settle into the pores of the ceramic in a stagnant environment for fifteen minutes. The pumps were turned on again as new cells entered the monolith. The monoliths were rotated ninety degrees and the pumps stopped for another fifteen minutes while cells were allowed to settle on the second side. This procedure was repeated until all four sides had been inoculated. At this point, both monoliths were positioned vertically and the cells were permitted to grow in a stagnant environment without medium flow for one hour.

E. Bioreactor Operation

Once both monoliths had been inoculated with hybridoma cells, fresh medium was supplied at rates high enough to ensure low waste product concentrations. Medium feed rates were measured with a stopwatch and 0.5 mL pipettes that were connected to each feed line. Air flow rates through the silicone tubes in the single-pass bioreactor were measured as the rate of water displacement from a volumetric flask. Air flow through the silicone tubes was maintained at a rate of two hundred and sixty seven cubic centimeters per minute at a pressure in the range of between about three and five pounds per square inch (gauge pressure).

Samples were taken periodically during the transient phase from the exit of the single-pass bioreactor and from the central medium reservoir of the recycle bioreactor. Both samples were centrifuged at 350 times the force of gravity for ten minutes and the supernatant stored frozen in one milliliter aliquots at −70° C. for subsequent nutrient- and product-assays.

Once both bioreactors had achieved a steady-state operation, as evidenced by a constant glucose consumption rate and a constant lactate and IgG production rates, experiments were performed to determine steady-state concentrations over a range of reactor residence times. Feed rates were changed in a step-wise manner, and samples were taken after at least five residence times had passed. Step changes were arbitrary at low residence times in both bioreactors. At higher residence times, however, waste product concentrations were above inhibitory levels: feed rates in this range were decreased sequentially to avoid possible hysteresis effects due to low culture viability in areas where waste product concentrations were high.

F. Assays

Glucose and lactate concentrations were determined enzymatically using glucose-6-phosphate dehydrogenase and lactate dehydrogenase, respectively, commercially available from Sigma Chemical Co. Murine immunoglobulin IgG concentrations were measured with the ORIGEN assay system, commercially available from IGEN, Inc. This assay was based on a homogeneous competition for goat anti-mouse antibody between labeled IgG and sample IgG. The label was ruthenium tris(bipyridine), which luminesces when electrochemically excited in solution. The electrochemiluminescence of bound labeled IgG is attenuated relative to unbound labeled IgG.

G. Results

Table I summarizes the dimensions of both types of bioreactors investigated in this side-by-side experiment.

TABLE I

|  | Single-Pass | Recycle |
|---|---|---|
| Ceramic mass (g) | 12.3 | 15.7 |
| Number of Channels | 13 | 112 |
| Monolith length (cm) | 50.8 | 10.2 |
| Reactor volume (mL) | 32 | 205 |

The mass of ceramic used in both systems was comparable. The single-pass bioreactor was constructed using a long monolith with relatively few square channels running the length of the reactor, while the recycle bioreactor was constructed using a short monolith with many channels. The total liquid volume in the recycle bioreactor was 6.4 times greater than in the single-pass bioreactor. The reactor for such a large difference in the two volumes is that the recycle bioreactor requires a certain medium volume external to the monolith so that oxygen can be resupplied in the liquid before it reenters the monolith.

H. Recycle Bioreactor

Figure 10:
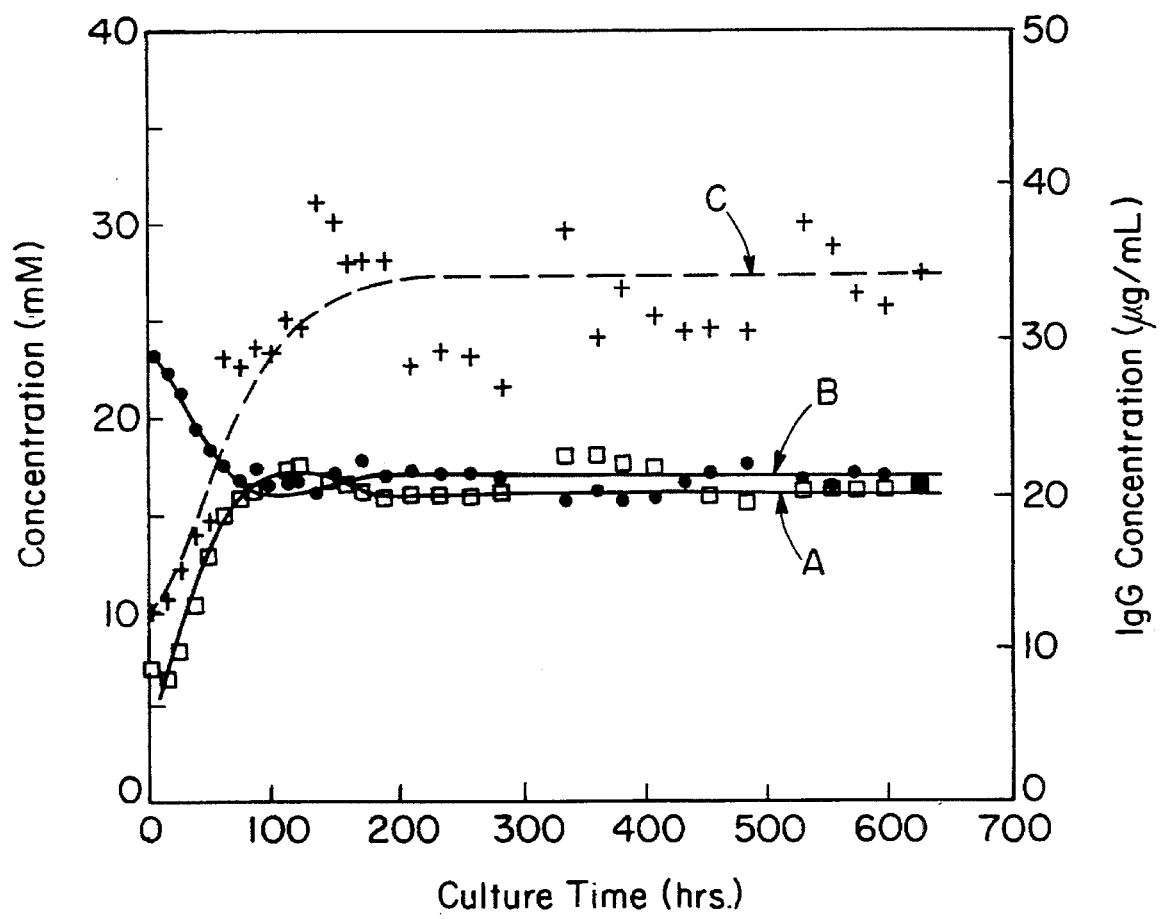
FIG. 10 is a plot of cell-product, cell waste-product and nutrient concentrations in medium recycled through a conventional recycle-type cell-culture system.

Glucose, lactate, and IgG monoclonal antibody concentrations are shown in FIG. 10 for the recycle bioreactor as a function of time since inoculation. The measured feed rate throughout this period averaged 0.51 ml/min. The transient approach to steady-state operation lasted 150–200 hours, after which time all measured concentrations appeared to be constant. Lactate, glucose and IgG concentrations, represented by curves A, B and C, respectively at steady-state were approximately 17 mM, 16 mM, and 34 µg/ml, respectively. The high glucose concentration and moderate lactate concentration in the medium indicate that the entrapped cells were not limited by nutrient concentrations, and waste product concentrations were below toxic levels.

Figure 11:
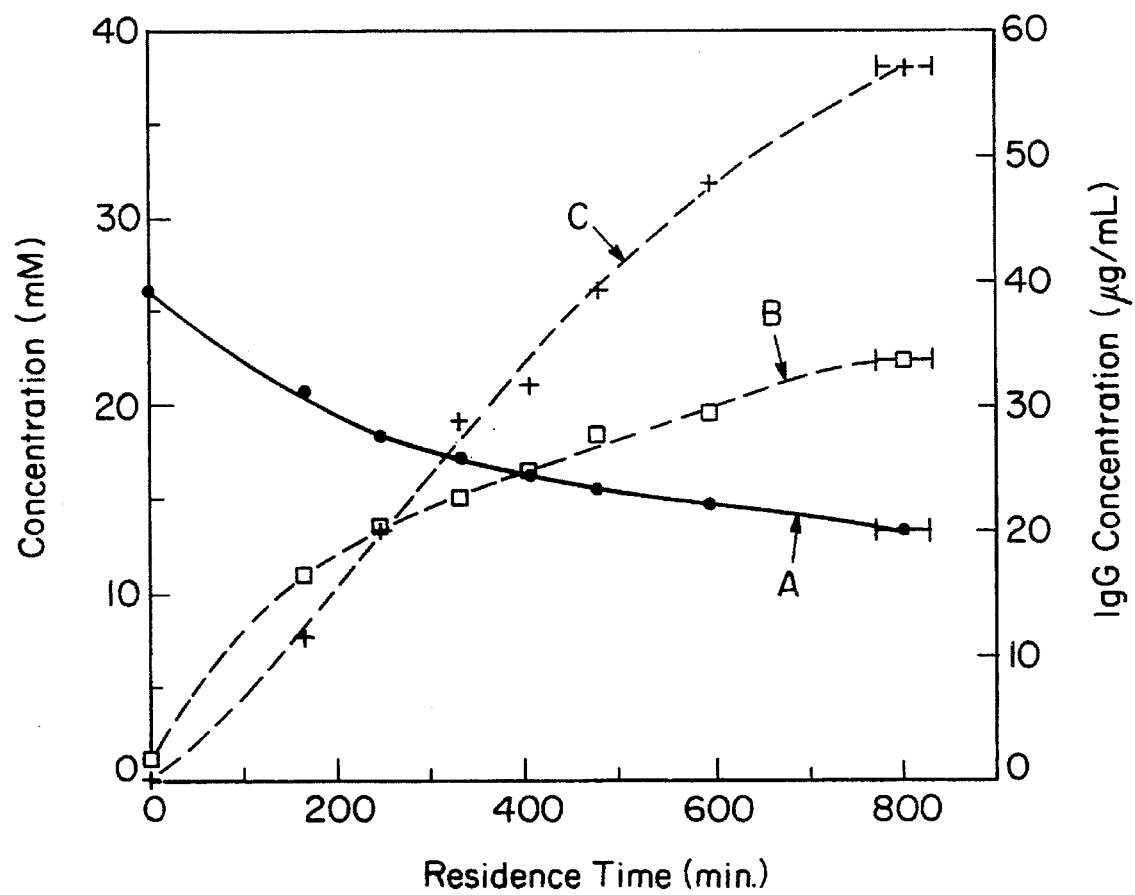
FIG. 11 is a plot of cell-product, cell waste-product and nutrient concentrations generated in a medium directed through a conventional recycle-type cell-culture system at steady state for various residence times of the medium within a cell-culture reactor of the cell-culture system.

After 625 hours of culture time, steady-state experiments were initiated to determine substrate and product concentrations at various operational residence times. The results of this experiment are shown in FIG. 11, where each data point represents the average of several measurements taken at steady state at that residence time. The qualitative characteristics of each curve follow expected behavior. Glucose concentration, represented by curve A, decreased smoothly as average residence time increased, and both lactate and IgG concentrations, represented by curves B and C, respectively, increased with increasing residence time. The highest antibody concentration was achieved at 800 hours residence time and was measured to be 57 μg/mL. The corresponding lactate concentration was determined to be 22 mM, a value generally considered to be about the limit for maintaining reasonable culture viability. At longer residence times, it was expected that cell viability would be so low throughout the bioreactor that the rate of antibody production would fall off dramatically.

I. Single-Pass Bioreactor

Figure 12:
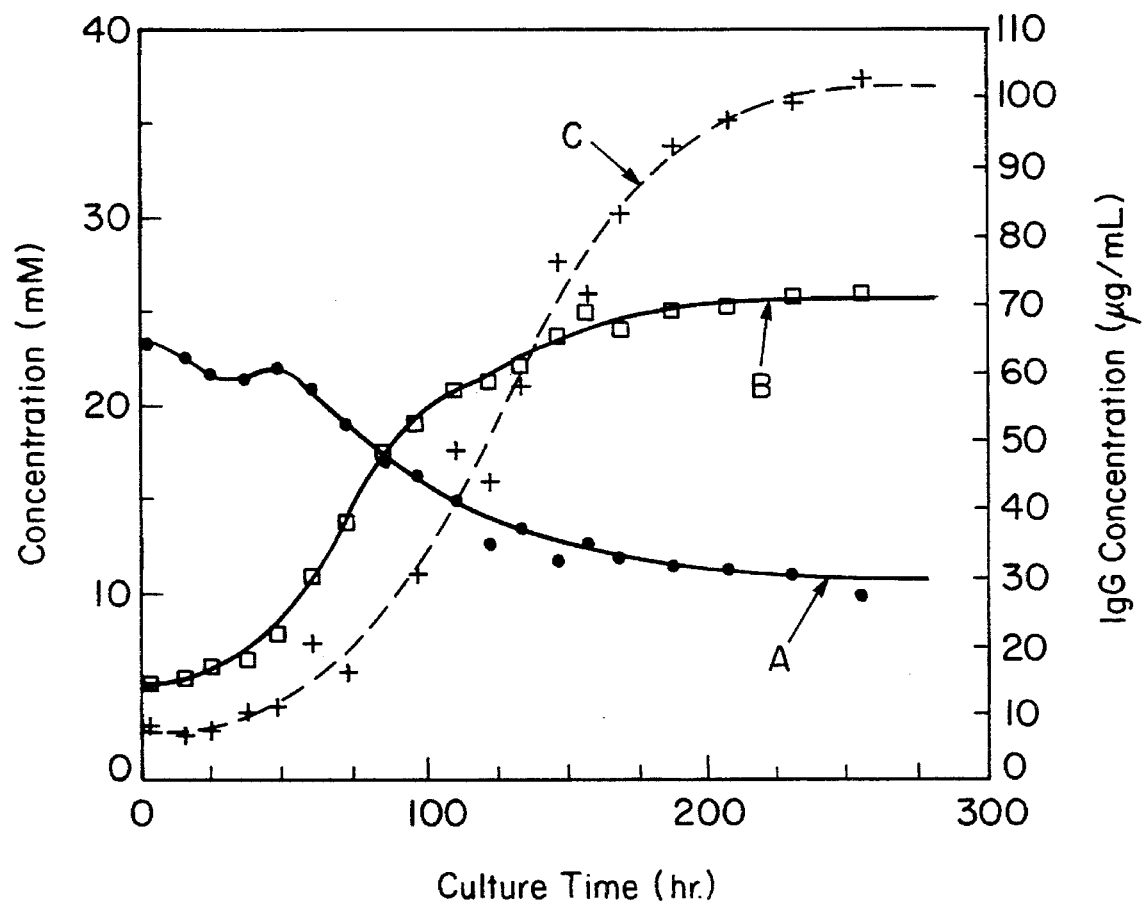
FIG. 12 is a plot of cell-product, nutrient, and cell waste-product concentrations over time in medium exiting a cell-culture reactor of the embodiment of the invention shown in FIG. 3.

FIG. 12 shows glucose, lactate and IgG concentrations, represented as curves A, B and C, respectively, during the transient approach to steady state for the single-pass bioreactor operation. Medium feed rate was maintained at 0.27 ml/min, and air flow rate through the silicone tubing was 267 cc/min throughout this period. It can be seen that all measured concentrations level off to constant values after approximately 200 hours, indicating that the bioreactor had entered its steady-state phase at that point. There appears to be a lag phase at the start of the run that lasted about 50–75 hours. The reason for this lag probably stems from the fact that no $CO_2$ was present in the gas stream flowing through the bioreactor. Visual observation by way of the phenol red indicator confirmed that the medium pH was significantly higher than normal during this period. Only when a reasonable entrapped cell concentration was attained did pH return to a physiological range.

Residence time through the bioreactor during the transient period was 120 min. It is evident from FIG. 12 that sufficient oxygen was supplied to the culture such that neither cell growth nor antibody production was adversely affected in this experiment. The growth phase compares well with the recycle bioreactor transient growth phase: in both cases this phase lasted 150–200 hours. Final lactate and IgG concentrations are significantly higher for the single-pass reactor, indicating that high entrapped-cell concentrations had been achieved in the monolith. Furthermore, the residence time was so long that the bulk of the oxygen supply was the result of oxygenation through the silicone tubes, not from the medium entering at the base of the bioreactor.

Figure 13:
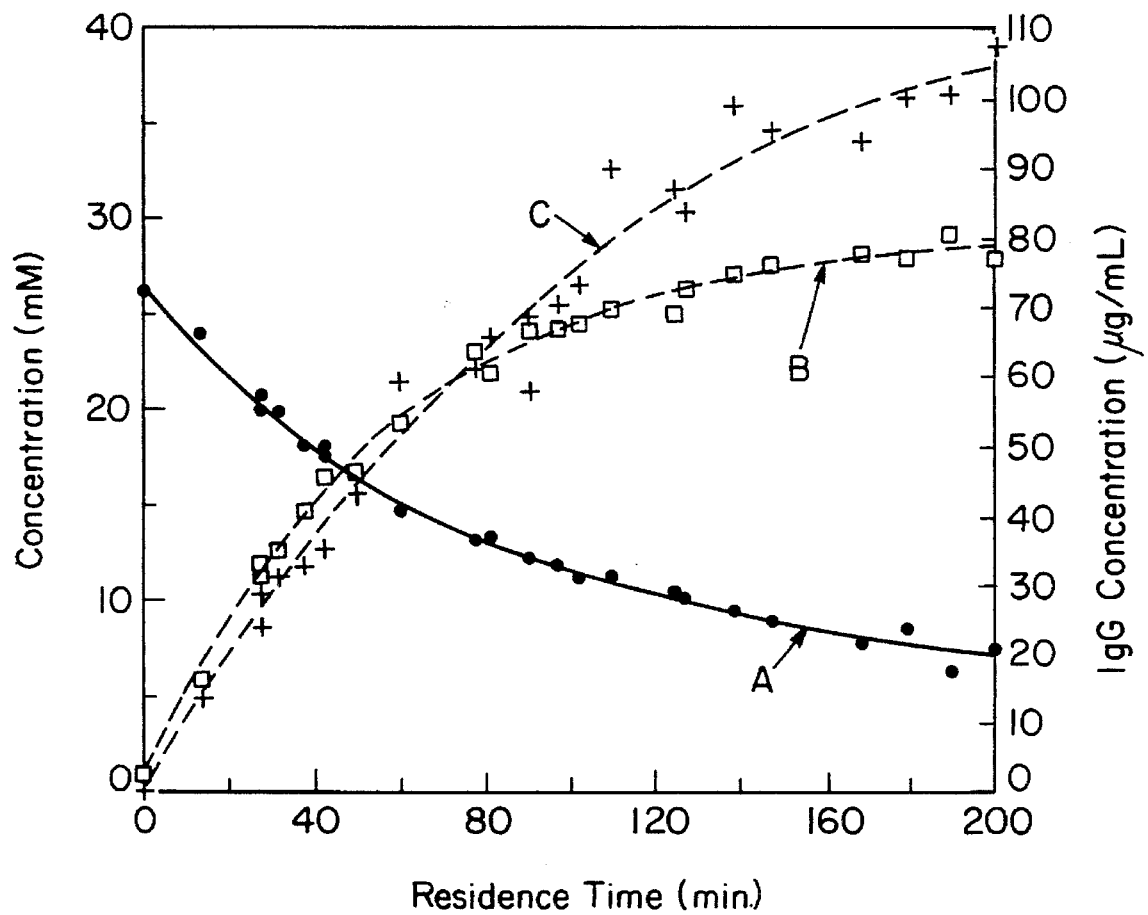
FIG. 13 is a plot of nutrients, cell waste-product and cell-product concentrations at steady state in medium exiting a cell-culture reactor of the invention for various residence times of the medium within the cell-culture reactor shown in FIG. 3.

Steady-state experiments were started after 280 hours of culture time. The results are shown in FIG. 13 where exit glucose, lactate, and antibody concentrations, represented as curves A, B and C, respectively, are plotted as a function of medium residence time through the monolith. All three curves show smooth behavior with monotonically decreasing consumption and production rates. At residence times less than 80 minutes, the curves are essentially linear. As waste product concentrations increase at higher residence times, the rate of increase in IgG titer slows. This can be attributed to a declining specific antibody productivity or a lower concentration of viable cells or both. Specific antibody productivity for this cell line is known to be inhibited by high lactate concentrations in the medium (Glacked, "Development of Mathematical Descriptions of Mammalian Cell Culture Kinetics for the Optimization of Fed-Batch Bioreactors," Ph.D. Thesis, Massachusetts Institute of Technology, Cambridge, Mass. (1987)). It was expected that, at longer residence times, antibody titer would level off to a constant value. Exit waste product concentrations would be expected to be well above toxic levels, and so all cells entrapped near the far end of the monolith would be non-viable.

J. Discussion

Figure 14:
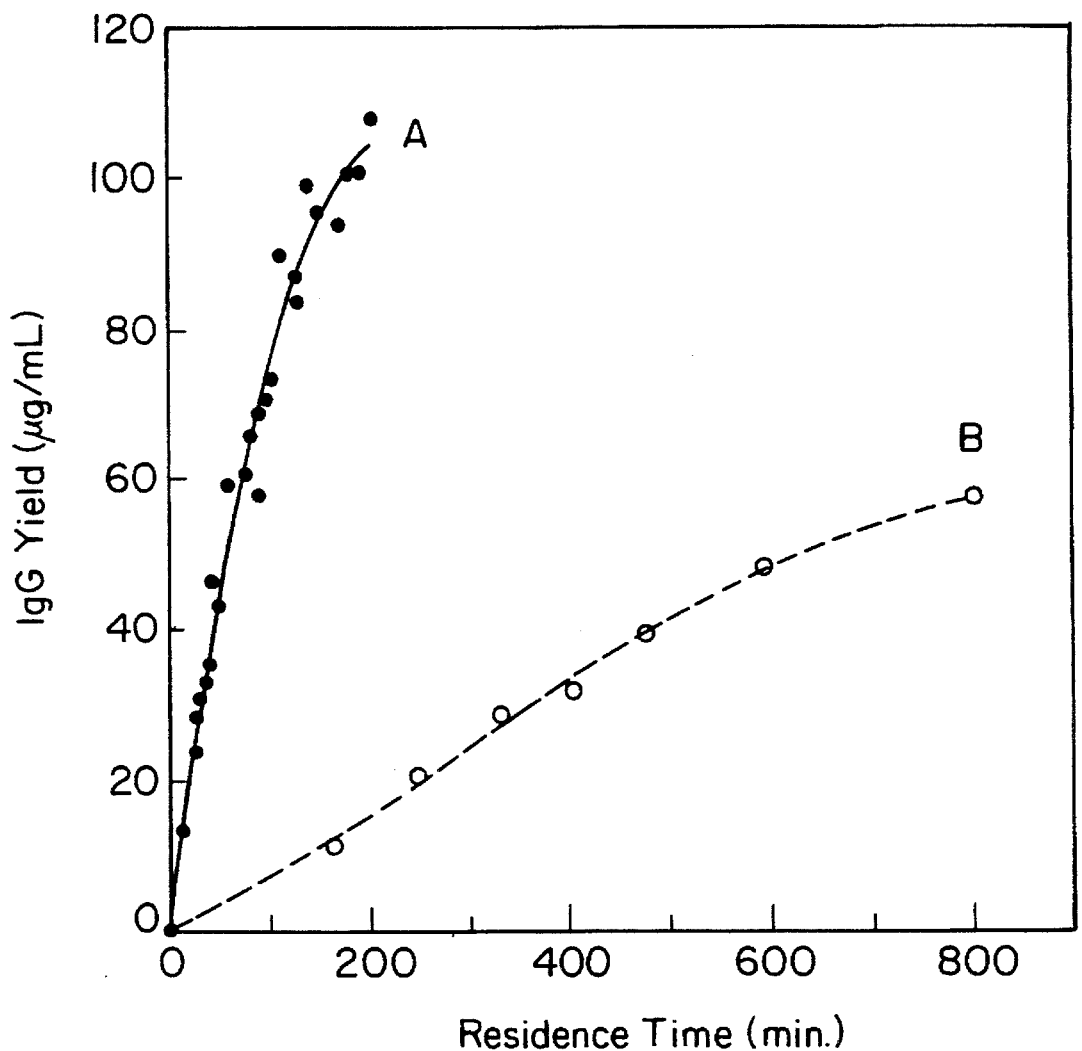
FIG. 14 is a plot of cell-product yield in micrograms per milliliter of medium leaving a conventional recycle-type cell-culture reactor and a plot of cell-product yield in medium leaving a cell-culture reactor of the embodiment of the invention shown in FIG. 3 at steady state of the cell culture for various residence times of the medium in the cell-culture reactors.

Steady-state antibody yield on medium consumed for single-pass and recycle bioreactors are replotted on the same graph in FIG. 14 and represented as curves A and B, respectively. It should be noted that yields are equivalent to concentrations for these reactors because there is no in situ concentration of product, as is the case of many hollow fiber bioreactors and some encapsulated systems. Final antibody yield was 80% higher for the single-pass bioreactor.

Since reactor volume in a single-pass reactor is much lower than that possible for recycle bioreactors, average residence times are lower as well. The difference in residence times depends on the ratio of total monolith volume to reactor medium volume. For a single-pass reactor, this ratio will be slightly greater than 1.0, owing to the presence of silicon tubing which displaces some liquid from the total monolith volume. The ratio of monolith volume to reactor medium volume for the single-pass bioreactor used in this experiment was 1.26:1. For a recycle bioreactor, a range of ratios is possible and the actual value depends on the scale under consideration. For laboratory-scale bioreactors such as the one used in this experiment, the ratio will be quite low. The calculated ratio for the present recycle bioreactor was 0.24. For a production-scale bioreactor, a realistic value of the ratio of monolith volume to reactor medium volume is 0.40. Thus, residence times for the single-pass bioreactor presented here are likely to be 30–50% of the residence that a corresponding large-scale recycle bioreactor can achieve. Combined with the enhancement in product titer, the single-pass, plug-flow bioreactor represents a five-fold increase in volumetric productivity over a typical production-scale recycle bioreactor.

Equivalents

Those skilled in the art will recognize, or be able to ascertain using no more than routine experimentation, many equivalents to specific embodiments of the invention described specifically herein. Such equivalents are intended to be encompassed in the scope of the following claims.

We claim:

1. An apparatus for culturing cells, comprising:

a) a cell-culture reactor having a cell-culture medium inlet and a cell-culture medium outlet;

b) a monolithic biocompatible macroporous support defining a passage, said support disposed within the cell-culture reactor between the medium inlet and the medium outlet, wherein the monolithic biocompatible macroporous support includes pores which have a pore diameter sufficient to allow cells of a cell culture to collect within the pores and to allow oxygen and other nutrients to migrate from the passage into the pores for consumption by the cells;

c) at least one oxygen-permeable conduit disposed within the passage, whereby oxygen in an oxygen-containing gas directed through the oxygen-permeable conduit migrates from the oxygen-containing gas across an oxygen-permeable wall of the oxygen-permeable conduit and is dissolved in cell-culture medium directed through the passage, thereby allowing oxygen to migrate from the passage to the cell culture within the pores of the monolithic biocompatible macroporous support;

d) means for directing the oxygen-containing gas through the oxygen-permeable conduit, whereby oxygen migrates across the oxygen-permeable wall of the oxygen-permeable conduit to the cell-culture medium which is being directed through the passage within the cell-culture reactor; and e) means for directing the cell-culture medium from the medium inlet through the passage within which the oxygen-permeable conduit is disposed and out of the cell-culture reactor at the medium outlet at a rate sufficient to provide nutrients to the cells in the pores of the monolithic biocompatible macroporous support in an amount sufficient to culture the cells.

2. An apparatus of claim 1 further comprising means for collecting and removing cells from the cell-culture reactor during culturing of the cells.

3. An apparatus of claim 2 wherein the monolithic biocompatible macroporous support comprises a plurality of walls which define the passage and wherein the passage is elongate and substantially straight.

4. An apparatus of claim 3 wherein the pores of the monolithic biocompatible macroporous support have an average pore diameter in the range of between about five microns and about two hundred microns.

5. An apparatus of claim 4 wherein at least a portion of the pores extend through the walls.

6. An apparatus of claim 5 wherein the oxygen-permeable conduit includes a tube.

7. An apparatus of claim 6 further including at least one intermediate medium inlet port and at least one intermediate medium outlet port disposed along the cell-culture reactor between the medium-inlet and the medium-outlet.

8. An apparatus of claim 7 wherein the monolithic biocompatible macroporous support includes a polymer.

9. An apparatus of claim 7 wherein the monolithic biocompatible macroporous support includes magnesium aluminate.

10. An apparatus of claim 7 wherein the monolithic biocompatible macroporous support includes hydroxyapatite.

11. An apparatus of claim 7 wherein the monolithic biocompatible macroporous support includes cordierite.

12. An apparatus of claim 11 wherein the oxygen-permeable conduit includes silicone tubing.

13. A method of culturing cells, comprising the steps of:

a) inoculating a monolithic biocompatible macroporous support disposed within a cell-culture reactor having a cell-culture medium inlet and a cell-culture medium outlet, the monolithic biocompatible macroporous support defining a passage between the medium inlet and the medium outlet, the monolithic biocompatible macroporous support including pores having a pore diameter sufficient to allow cells to collect within the pores and to allow oxygen and other nutrients to migrate from the passage into the pores for consumption by the cells;

b) directing a cell-culture medium into the medium inlet at a rate sufficient to provide nutrients to the cells in the pores of the monolithic biocompatible macroporous support in an amount sufficient to culture the cells; and c) directing an oxygen-containing gas through an oxygen-permeable conduit disposed within the passage, whereby oxygen in the oxygen-containing gas migrates across an oxygen-permeable conduit to the cell-culture medium which is being directed through the passage, thereby allowing oxygen to migrate from the passage to a cell culture within the pores of the monolithic biocompatible macroporous support at a rate sufficient to culture the cells.

14. A method of claim 13 wherein the cell-culture medium is directed through the passage in a single pass of the cell-culture medium.

15. A method of claim 14 further including the step of directing the cell-culture medium into the passage at a point between the medium inlet and the medium outlet.

16. A method of claim 15 further including the step of withdrawing spent medium from the passage at a point between the medium inlet and the medium outlet.

17. A method of claim 16 further including the step of causing cells cultured in the cell culture reactor to collect within the cell-culture reactor at a point outside of the pores of the monolithic biocompatible macroporous support for removal of the collected cells from the cell-culture reactor.

18. In a method of culturing cells in a cell-culture reactor having a monolithic biocompatible macroporous support disposed within the cell-culture reactor and defining a passage through which cell-culture medium is directed:

The improvement comprising directing an oxygen-containing gas through an oxygen-permeable conduit disposed within the passage, whereby oxygen in the oxygen-containing gas migrates across an oxygen-permeable wall of the oxygen-permeable conduit to the cell-culture medium which is being directed through the passage, thereby allowing oxygen to migrate within the medium to a cell culture within pores of the monolithic biocompatible macroporous support at a rate sufficient to culture the cells.

\* \* \* \* \*

UNITED STATES PATENT AND TRADEMARK OFFICE
CERTIFICATE OF CORRECTION

PATENT NO. : 5,510,262
DATED : April 23, 1996
INVENTOR(S) : Gregory Stephanopoulos, Mark A. Applegate, Rahul Singhvi, Seujeung Park and Maria Flytzani-Stephanopoulos It is certified that error appears in the above-indentified patent and that said Letters Patent is hereby corrected as shown below:

In Column 1, before "Background of the Invention", insert:

--GOVERNMENT FUNDING

This invention was made with government support under Grant No. CDR 880 3014 by the National Science Foundation. The government has certain rights in the invention.--

Signed and Sealed this

Eighth Day of October, 1996

Attest:

BRUCE LEHMAN

*Attesting Officer*       *Commissioner of Patents and Trademarks*